United States Patent [19]

Ubukata et al.

[11] Patent Number: 5,028,228
[45] Date of Patent: Jul. 2, 1991

[54] APPARATUS FOR MAKING DENTAL ROOT CANAL FILLING POINTS

[75] Inventors: Noboru Ubukata, Kiryu; Hisao Iizuka, Ashikaga, both of Japan

[73] Assignees: G-C Dental Industrial Corp., Tokyo; Nimikagakukogyo Co., Ltd., Kiryu, both of Japan

[21] Appl. No.: 330,279

[22] Filed: Mar. 29, 1989

[30] Foreign Application Priority Data

Apr. 7, 1988 [JP] Japan .................................. 63-85592

[51] Int. Cl.[5] ........................ B29C 43/02; A61C 5/02; B30B 11/18
[52] U.S. Cl. ........................................ 425/298; 72/89; 72/207; 100/153; 425/364 R; 425/367; 425/373; 425/392; 425/394; 425/402; 433/224
[58] Field of Search ............... 425/220, 235, 237, 267, 425/268, 298, 321, 322, 332, 362, 364 R, 367, 373, 392, 402, 394; 433/81, 224; 72/89, 94, 207, 220; 100/47, 153, 164, 168, 169

[56] References Cited

U.S. PATENT DOCUMENTS

| 674,419 | 5/1901 | Kinsman | 433/224 |
|---|---|---|---|
| 1,463,963 | 8/1923 | Miller | 433/224 |
| 1,757,595 | 5/1930 | Siegel | 433/224 |
| 2,218,460 | 10/1940 | Singer et al. | 72/207 |
| 3,233,444 | 2/1966 | Groves et al. | 72/207 |
| 4,525,147 | 6/1985 | Pitz et al. | 433/224 |

FOREIGN PATENT DOCUMENTS

| 62-3841 | 1/1987 | Japan | 72/89 |
|---|---|---|---|
| 846012 | 7/1981 | U.S.S.R. | 72/89 |
| 214497 | 4/1924 | United Kingdom | 433/224 |

Primary Examiner—James C. Housel
Attorney, Agent, or Firm—Oblon, Spivak, McClelland, Maier & Neustadt

[57] ABSTRACT

An apparatus for making a dental root canal filling point is provided, wherein provision is made of a rotary member having its outer processing surface in the form of a curved plane in parallel with its axial direction and adapted to be rotated at a predetermined speed and a moving member in which at least its processing surface is located in parallel with the processing surface of the rotary member and adapted to move at a speed substantially identical with a peripheral speed of the rotary member in the same direction as the rotational direction of the rotary member in a gap portion in which a minimum distance is defined between the processing surfaces of the rotary member and moving member. While at least the rotary member is rocked in its axial direction and the gap portion lies on a substantially identical plane, a rod-like material for the dental root canal filling point is fed in the gap portion between the processing surfaces of the rotary member and moving member to bring the leading end of the material in the gap portion in a direction normal to the axial direction of the rotary member, and a ratio of a moving speed of the leading end of the material brought in with respect to a moving speed at which the processing surfaces of the rotary member and moving member are spaced away from each other being continuously varied such that it conforms to a taper of the dental root canal filling point, thereby making the dental root canal filling point, which has the desired taper.

41 Claims, 11 Drawing Sheets

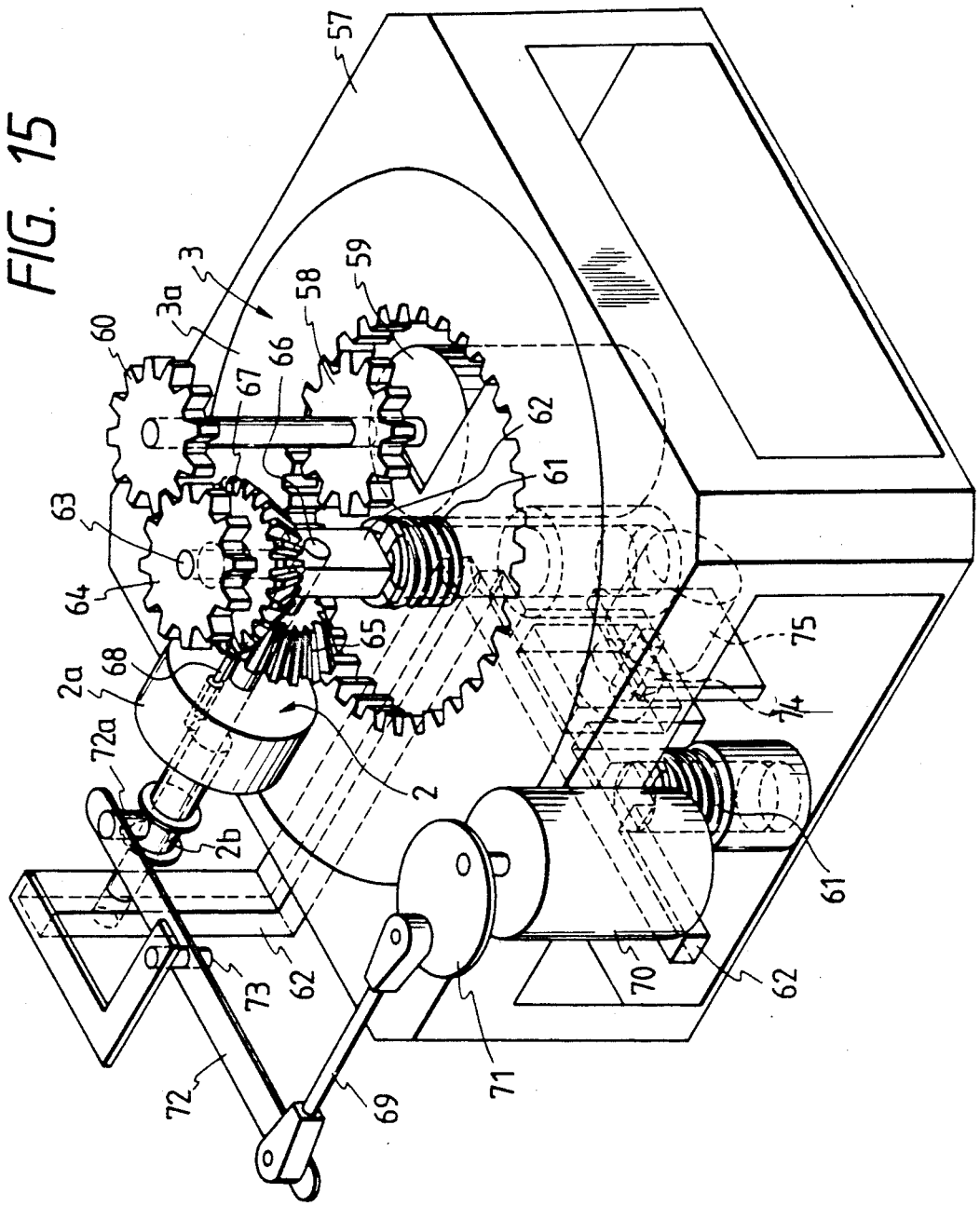

APPARATUS FOR MAKING DENTAL ROOT CANAL FILLING POINTS

BACKGROUND OF THE INVENTION

1. Field of the Invention

The present invention relates to a method and apparatus best-suited to make dental root canal filling points, which are formed of a thermoplastic material in the form of an elongated cone and which are used as a filling and obturating material or sealing material for pulp cavities formed after pulpectomy or the disinfection of infected root canals during dental treatments, inter alia, to make a dental root canal filling point referred usually to as a gutta-percha point, and an apparatus for making the same.

2. Statement of the Prior Art

Conventional dental root canal filling points usually called the gutta-percha points in the form of an elongated cone have been fabricated by cutting into a wedgy shape a thin, elongated and complanate material comprising a composition usually containing 60 to 70% of zinc oxide, 20 to 25% of refined gutta-percha, a heavy metal salt for improving radio-opacity and a small amount of wax, resin and the like, then heating and softening the material at about 80° C. and finally shaping the softened material into an elongated cone, while manually rolling it on a kneading plate with the use of a spatula.

By reason that the conventionally used gutta-percha points are prescribed in size and shape according to the standards of dental root canal instruments used for the preparation of root canals, however, the number of their types reach as many as 19 in terms of sizes of the international standards in particular, while severer dimensional tolerances of as small as ±0.04 mm is required for their diameters. Moreover, numerous types of products varying in diameter from a lowest 0.1 mm to a highest 1.5 mm in the length range of 10 to 35 mm are commercially available because various dental-root-canal-filling-point makers make nonstandardized products of their own in addition to the standardized ones. In orde :o make dental root canal filling points, the only option has been rely upon skilled workers. This has implied that it is necessary to train unskilled workers, and has posed a problem that it is difficult to meet an increased demand in the recent advancement of dental treatments.

In order to simplify the production of dental root canal filling points and increase the yield of products by mechanical means, molding processes with extruders and casting dies have been attempted. However, owing to much severer accuracies imposed upon the dimensions and shapes of the dental root canal filling points, as mentioned above, a cost problem arises with possible burring or failure of the products during the releasing of the product from the molds. As yet, there has been thus unavailable any method capable of mechanically mass-producing the dental root canal filling points. In consequence, the production of the dental root canal filling points is still carried out by man power. In that case, the efficiency of inspection of the products is very low, since all the products should individually be inspected after they have been broken down into as many standards as mentioned above. Worse yet, barely about 65% of the products are accepted due to a high probability of some products being misclassified and rejected even by those versed in the art, resulting in waste in the production, such has been the problems difficult to solve in the prior art.

Therefore, the present inventors have made intensive and extensive studies of how to carry out in a mechanical, simple and dimension-stable manner the production of the dental root canal filling points, which have been considered difficult to make by other means than manual ones and, as a result, have found out that the method to be described below enables them to be fabricated both efficiently and mechanically.

SUMMARY OF THE INVENTION

According to the present invention, there is provided a method for making a dental root canal filling point, wherein:

provision is made of a rotary member having its outer processing surface in the form of a curved plane in parallel with its axial direction and adapted to be rotated at a predetermined speed and a moving member in which at least its processing surface is located in parallel with said processing surface of said rotary member and adapted to move at a speed substantially identical with a peripheral speed of said rotary member in the same direction as the rotational direction of said rotary member in a gap portion in which a minimum distance is defined between said processing surfaces of said rotary and moving members, while at least said rotary member is rocked in its axial direction and said gap portion lies on a substantially identical plane, a rod-like material for said dental root canal filling point being fed in said gap portion between said processing surfaces of said rotary and moving members to bring the leading end of said material in said gap portion in a direction normal to said axial direction of said rotary member, and a ratio of a moving speed of said leading end of said material brought in with respect to a moving speed at which said processing surfaces of said rotary and moving members are spaced away from each other being continuously varied such that it conforms to a taper of said dental root canal filling point, thereby making said dental root canal filling point, which has the desired taper.

The present invention also relates to an apparatus for making dental root canal filling points, which comprises in combination: a first belt driven by a first geared pulley driven by a first motor placed on a base; a first pulley attached to a first shaft provided across a framework fixed onto the base and driven by the movement of the first belt; a moving member attached to the first shaft and having an outer processing surface in the form of a curved plane, the curved plane being parallel with an axial direction of the moving member and being rotatable together with the first pulley; a second belt driven by a second geared pulley attached to a second shaft provided across the base, the second geared pulley being in gear mesh with the first geared pulley; moving links positioned on both sides of the base and operatively connected to a cam follower, the cam follower being in engagement with a cam, the cam being rotatably driven by a second motor placed on the base, wherein rotation of the second motor causes rocking of the moving links on both sides of base in a direction normal to the first shaft; and a rotary body slidably attached to a further shaft and having an outer processing surface in the form of a curved plane.

BRIEF DESCRIPTION OF THE DRAWINGS

Several preferred embodiments of the present invention will now be explained exclusively but not specifically with reference to the accompanying drawings, in which:

FIG. 15 is a perspective view of a further embodiment of the apparatus for making the dental root canal filling points according to the present invention.

DETAILED EXPLANATION OF THE PREFERRED EMBODIMENTS

The method for making the dental root canal filling points according to the present invention will now be explained in more detail.

Figure 1:
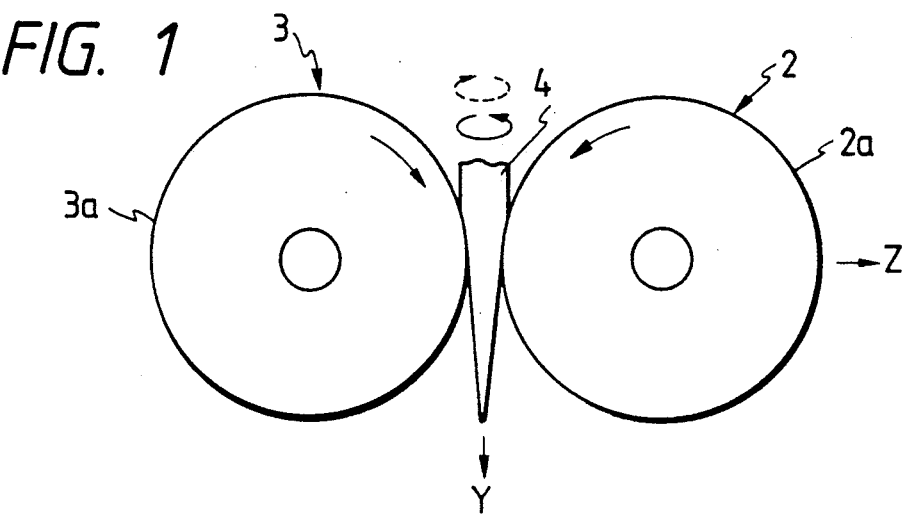
FIG. 1 is a view illustrating one embodiment of the method for making the dental root canal filling points according to the present invention.
Figure 2:
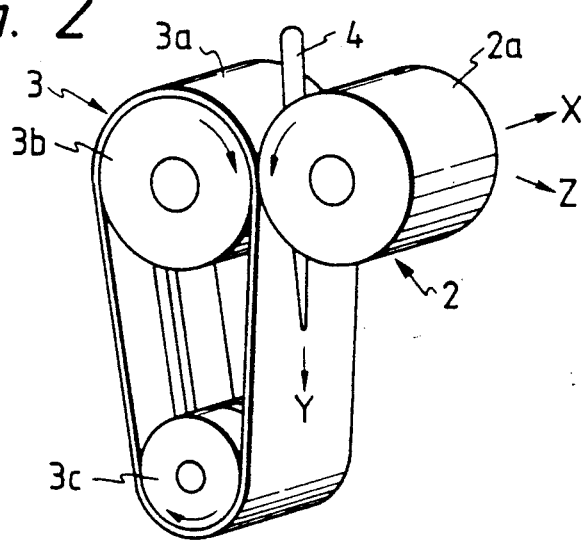
FIGS. 2, 3 and 4 are views showing another embodiment of the present method, in which the moving member is in the form of a curved plane.
Figure 3:
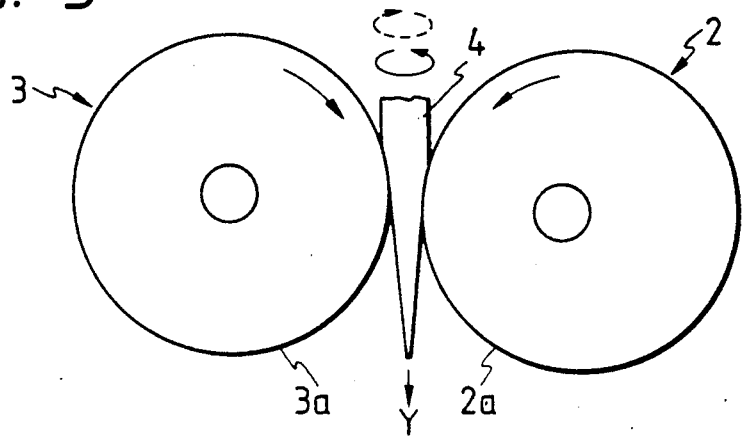
Figure 4:
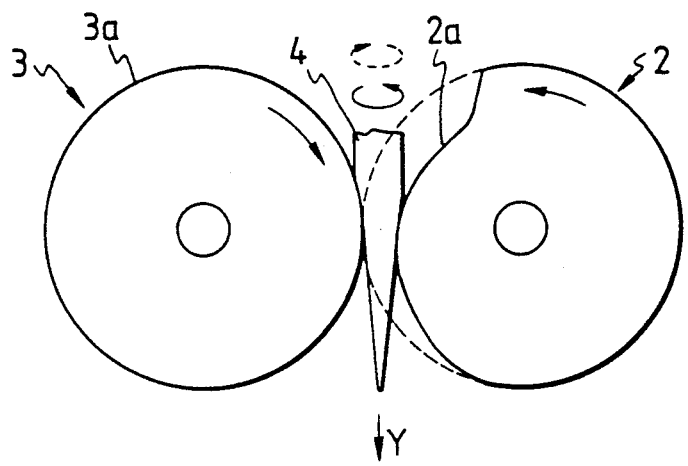
Figure 5:
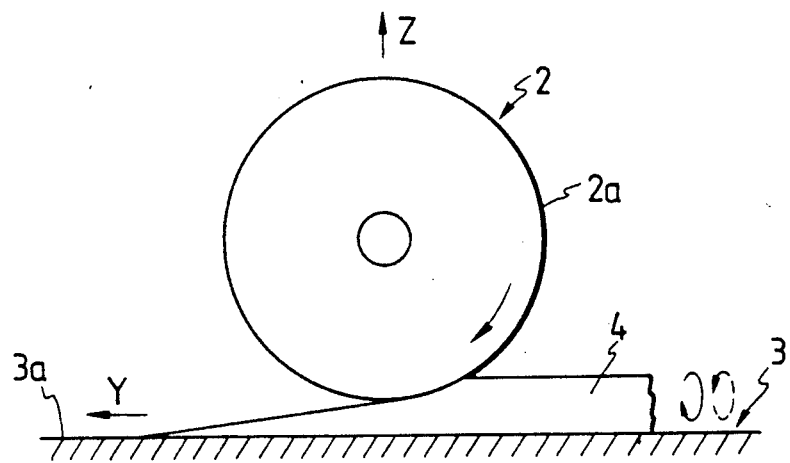
FIGS. 5, 6 and 7 are views showing a further embodiment of the present method, in which the moving member is in the form of a flat plane.
Figure 6:
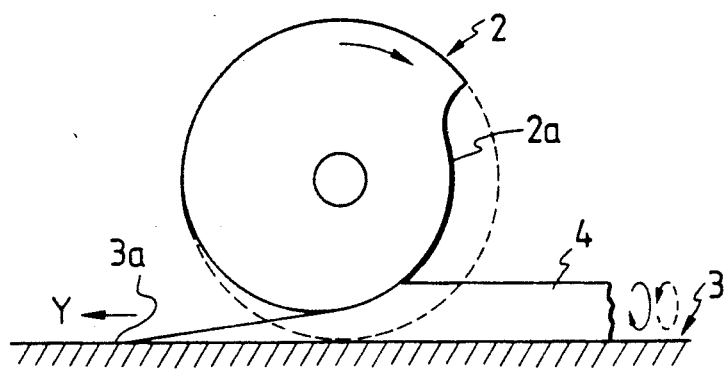
Figure 7:
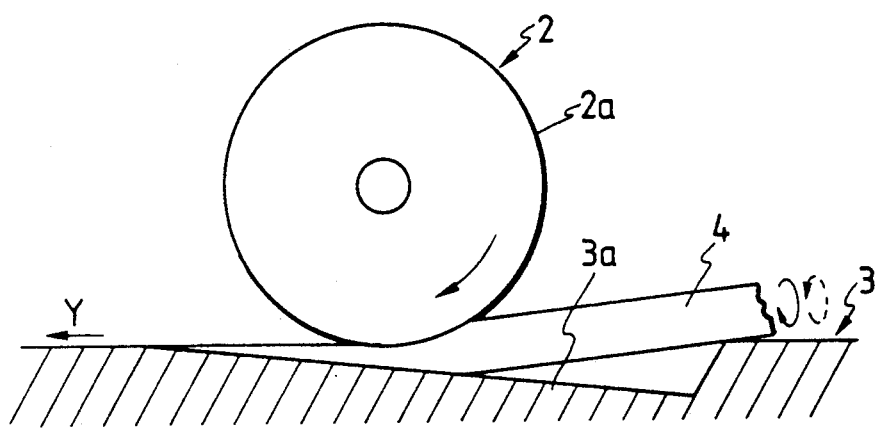
Figure 8:
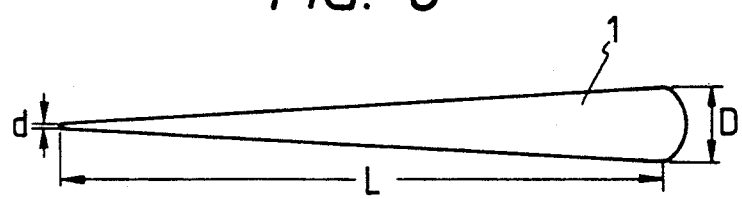
FIG. 8 is an enlarged front view of one example of the dental root canal filling point to be fabricated.

FIG. 1 is a view for illustrating the method for making the dental root canal filling points according to the present invention, FIGS. 2, 3 and 4 are views for illustrating another embodiment of the present method, in which the moving member is in the form of a curved plane, FIGS. 5, 6 and 7 are views for illustrating still another embodiment of the present method, in which the moving member is in the form of a flat plane, and FIG. 8 is an enlarged front view showing one example of the dental root canal filling point fabricated according to the present method.

Referring to the drawings, a dental root canal filling point 1 is in the form of an elongated cone, as shown in FIG. 8, is formed of a rod-like thermoplastic material for the dental root canal filling point such as, for instance, a composition comprising 60 to 70% of zinc oxide, 20 to 25% of refined gutta-percha, a heavy metal salt for improving radio-opacity and a small amount of wax, resin and the like or a composition which comprises polymer components of trans-1,4-polyisoprene and an ethylene/vinyl acetate copolymer resin and an insoluble or sparingly soluble inorganic filler and may contain organic components, as disclosed in Japanese Patent Laid-Open No. 62-61909. The dental root canal filling point 1 is available in various types wherein d is the diameter of its leading end, D is the diameter of its terminating end and L is the full length from d to D. In the present invention, the dental root canal filling point 1 is expressed in terms of the taper value defined by the following equation: $T=(D-d)/L$. A rotary member 2 has its outer processing surface 2a parallel with an axial direction X and taking on a curved plane, and is designed to rotate at a predetermined speed. The rotary member 2 used may be a cylindrical rotary body having its center of rotation coincident with its axis, as shown in FIGS. 1, 2, 5 and 7, a cylindrical rotary body having its axis located at an off-center position, as shown in FIG. 3, or a non-cylindrical rotary body whose distance from the axis to processing surface 2a varies successively. A moving member 3 is provided in such a way that at least its processing surface 3a is located in parallel with the processing surface 2a in a gap portion in which a distance between it and that processing surface 2a is minimized, and moves at a speed substantially equal to a peripheral speed of the rotary member 2 (i.e., a moving speed of the processing surface 2a) and in the rotational direction of the rotary member 2. The moving member 3 used may be a cylindrical rotary body having its center of rotation coincident with its axis, as shown in FIGS. 1, 3 and 4, or a belt driven along a cylindrical rotary body 3b having its center of rotation coincident with its axis, as shown in FIG. 2. Where the moving member 3 defined by such a belt as illustrated in FIG. 2 is used, it is supported by and between two cylindrical rotary bodies 3b and 3c. It is thus preferred that in order to prevent their jigzag movement, the cylindrical rotary bodies 3b and 3c be grooved in their outer surfaces and the moving member 3 defined by the belt be correspondingly provided with ribs to engage within such grooves. In a further embodiment, the moving member 3 used may have its processing surface 3a entirely flattened as illustrated in FIGS. 5 and 6, or its processing surface 3a defined by a flat plane having therein a groove inclining with respect to its moving direction, as shown in FIG. 7. Where the moving member 3 is the form of a flat plane as shown in FIGS. 5 to 7, it may be in the form of an endless belt, a flat plane which reciprocates simply, or a disc or wheel which rotates around its axis.

In the present invention, it is required that of the rotary member 2 and moving member 3, at least the rotary member 2 be rocked in the direction of its axis X. It is preferable to rock both the rotary member 2 and moving member 3, since the rocking stroke and speed are then decreased in half with the resulting effect being similar to that achieved by the rocking of one member. In addition, the resulting dental root canal filling points 1 are stable in position and of satisfactory shape. In the present invention, while the gap portion in which the minimum distance is defined between the processing surfaces 2a and 3a of the rotary member 2 and moving member 3 is located on a substantially identical plane, the rod-like material 4 for the dental root canal filling point is supplied in such a manner that it is brought into said gap between the processing surfaces 2a and 3a of the rotary member 2 and moving member 3 in a direction Y normal to the axial direction X of the rotary member 2, and the distance of said gap portion is continuously varied in a direction Z normal to both said directions X and Y in such a way that the speed ratio of the movement of the leading end of the material 4 brought in with the movement of the rotary member 2 and moving member 3 spaced away from each other is equal to the taper T of the point 1 to be produced. The rod-like material 4 for the dental root canal filling point supplied in the gap portion in which the minimum distance is defined between the processing surfaces 2a and 3a of the rotary member 2 and moving member 3 may be previously immersed in a hot water tank for softening. In order to increase the production efficiency of the dental root canal filling point 1, however, it is preferred to supply the rod-like material 4 for the dental root canal filling point, as mentioned above, while heated by one or more of means for blowing of heated air, irradiation of thermal energy from an infrared lamp or heating of the processing surfaces 2a and 3a of the rotary member 2 and moving member 3 with a band heater, etc., since that material 4 is usually softened when heating to about 45° C. While remaining softened in this manner, the material 4 for the dental root canal filling point is formed into a predetermined shape in the gap portion in which the minimum distance is defined between the processing surfaces 2a and 3a of the rotary member 2 and moving member 3. More preferably, just after passing through said gap portion, the leading end of that material 4 is cooled in order to prevent it from remaining softened and undergoing deformation.

Thus, provision is made of the rotary member 2 and the moving member 3 in such a way that at least the processing surface 3a of the moving member 3 is located in parallel with the processing surface 2a of the rotary member 2 and moves at a speed substantially equal to the peripheral speed of the rotary member 2 and in the same direction as the rotational direction of the rotary member 2 in the gap portion in which the minimum distance is defined between the processing surfaces 2a and 3a of the rotary member 2 and moving member 3. When at least the rotary member 2 is rocked in the axial direction X, the rod-like material 4 for the dental root canal filling point is supplied into the gap portion which is located on a substantially identical plane and in which the minimum distance is defined between the processing surfaces 2a and 3a of the rotary member 2 and moving member 3, and is then formed into a circular section having a diameter in coincidence with the distance of that gap portion.

The gap portion in which the minimum distance is defined between the processing surfaces 2a and 3a of the rotary member 2 and moving member 3 is continuously varied in distance in such a way that the speed ratio of the movement of the leading end of the rod-like material 4 for the dental root canal filling point brought in said gap portion by the movement of the rotary member 2 and moving member 3 moving in said gap portion at a substantially identical speed in the same direction with the movement of the rotary member 2 and moving member 3 spaced away from each other conforms with the taper T of the dental root canal filling point to be fabricated, whereby the material 4 for the dental root canal filling point is formed into the dental root canal filling point 1 which has the desired taper T in its longitudinal direction, while retaining a circular section. In order to continuously vary the distance of the gap portion in which the minimum distance is defined between the processing surfaces 2a and 3a of the rotary member 2 and moving member 3, it is required to provide means for spacing the rotary member 2 away from the moving member 3 and the moving member 3 away from the rotary member 2 in the case where, as shown in FIGS. 1, 2 and 5, the rotary member 2 is in the form of a cylindrical rotary body having its center of rotation coincident with its axis and the moving member 3 is in the form of a cylindrical rotary body having its center of rotation coincident with its axis, as is the case with the rotary member 2, or in the form of an entirely flat plane. However, such means may be dispensed with in the case where the rotary member 2 is in the form of a non-cylindrical rotary body 2 whose distance from the axis to processing surface 2a varies successively, as shown in FIG. 4 or 6, or a cylindrical rotary body 2 having its axis located at an off-center position as shown in FIG. 3, or the moving member 3 is in the form of a flat plane having its processing surface 3a provided therein with a groove inclining with respect to its moving direction, as illustrated in FIG. 7. This is because mere rotation of the rotary member 2 around its center of rotation causes the rod-like material 4 for the dental root canal filling point to be brought by the relative movement of the processing surfaces 2a and 3a of the rotary member 2 and moving member 3 in the gap portion in which the minimum distance is defined therebetween, while said gap portion is located on a substantially identical plane, thereby continuously varying the distance of said gap portion in such a way that the speed ratio of the movement of the leading end of that material 4 with respect to the movement of the rotary member 2 and moving member 3 spaced away from each other is in coincidence with the taper T of the dental root canal filling point 1 produced.

Reference will now be made to one embodiment of the apparatus for making the dental root canal filling points according to the present invention.

Figure 9:
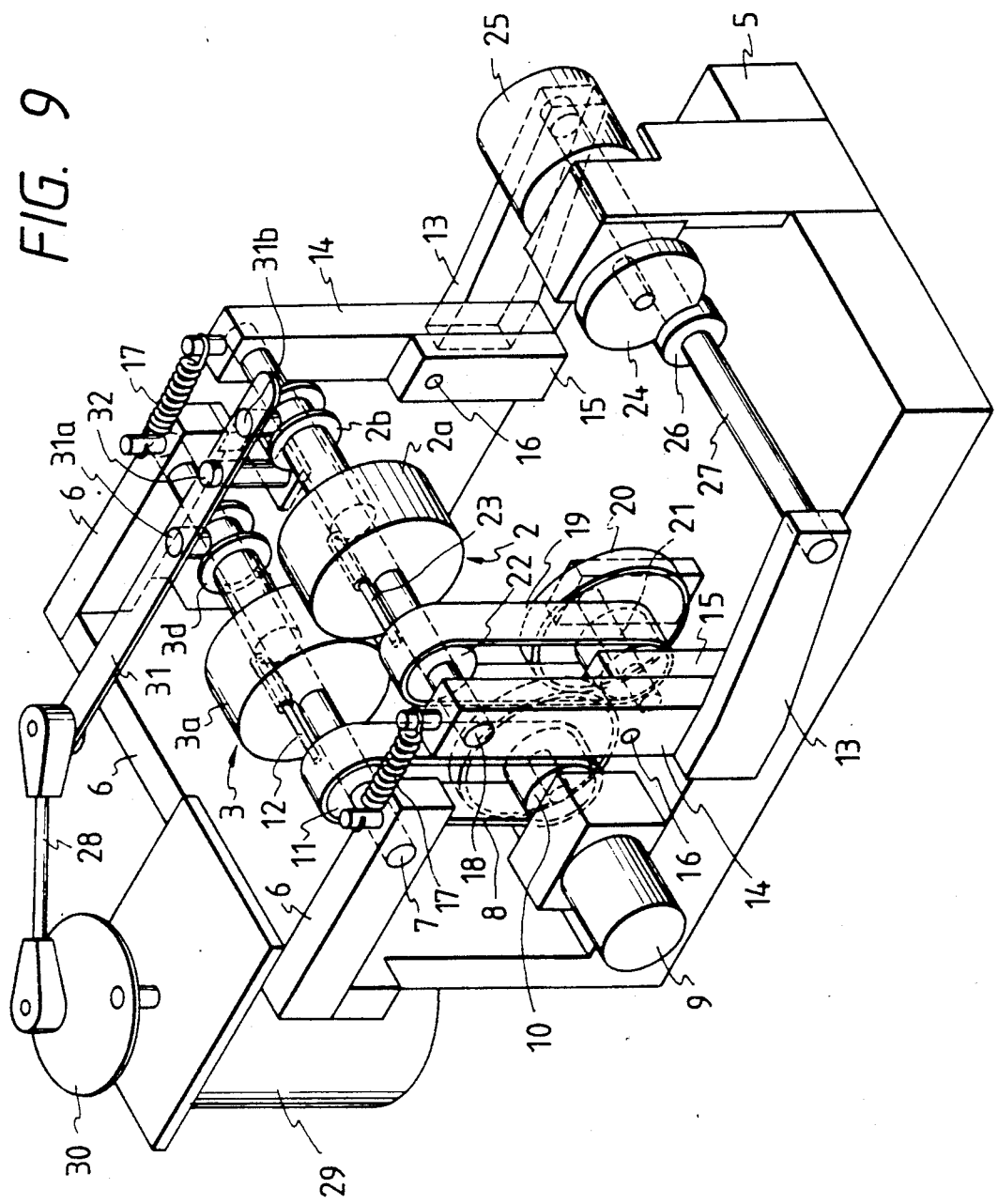
FIG. 9 is a perspective view of one embodiment of the apparatus for making the dental root canal filling points according to the present invention.
Figure 10:
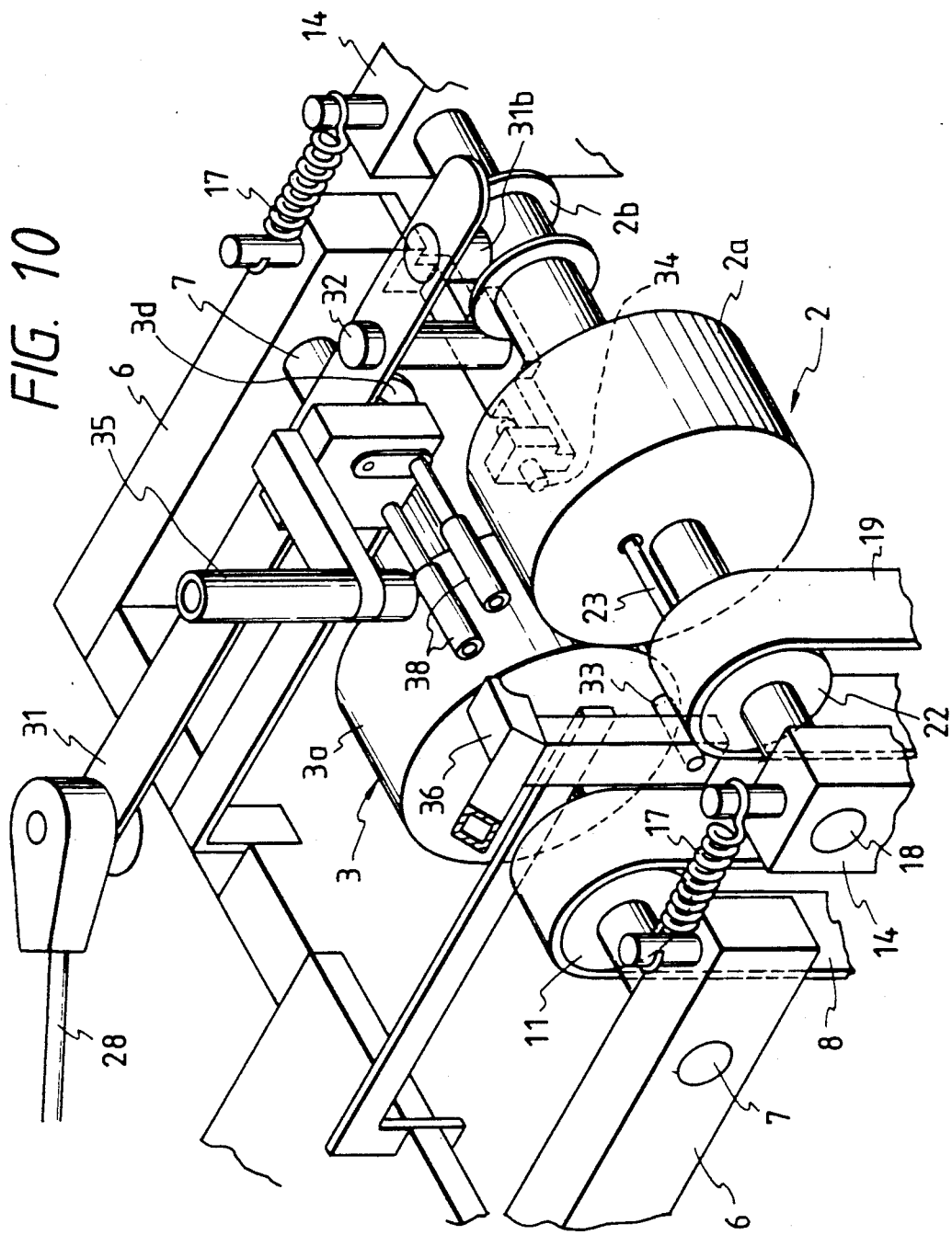
FIG. 10 is an enlarged perspective view of part of that embodiment.
Figure 11:
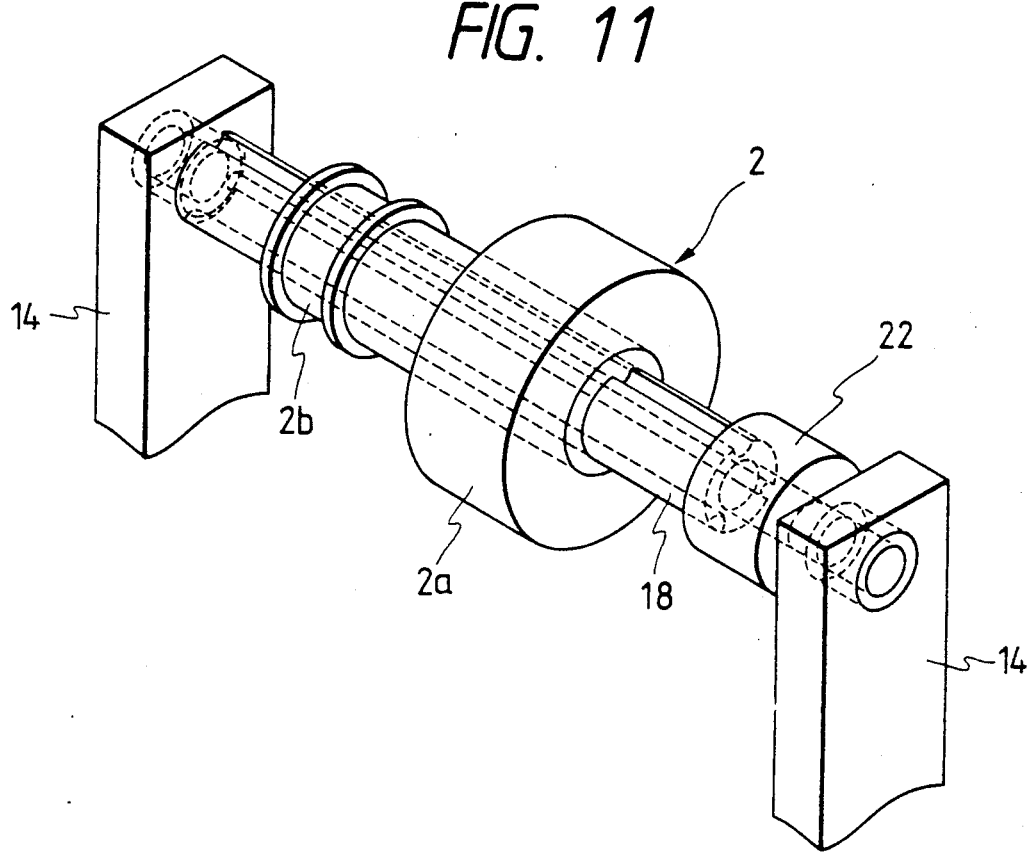
FIG. 11 is a perspective view of another embodiment of the rocking rotary member which is attached in place.
Figure 12:
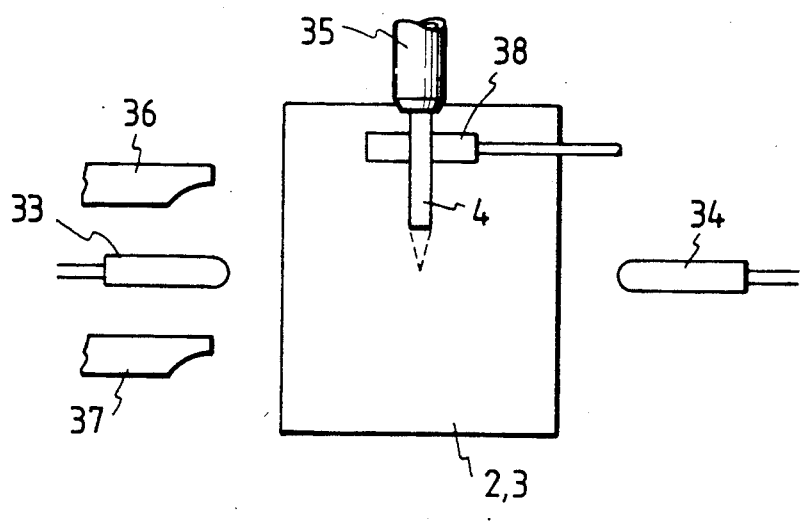
FIG. 12 is a view illustrative of the initial stage of the fabrication of the dental root canal filling points with the present apparatus as shown in FIG. 9.
Figure 13:
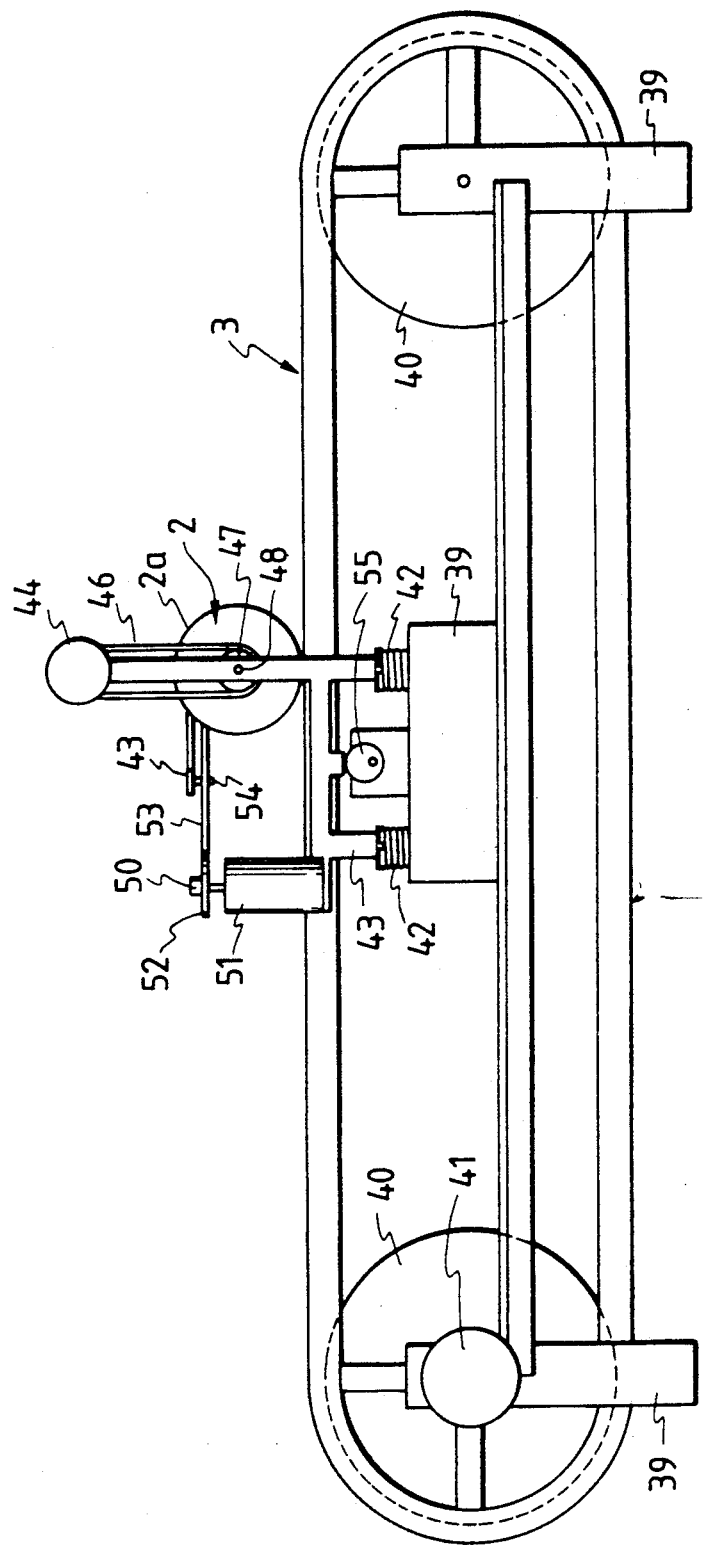
FIG. 13 is a perspective view of another embodiment of the apparatus for making the dental root canal filling points according to the present invention.
Figure 14:
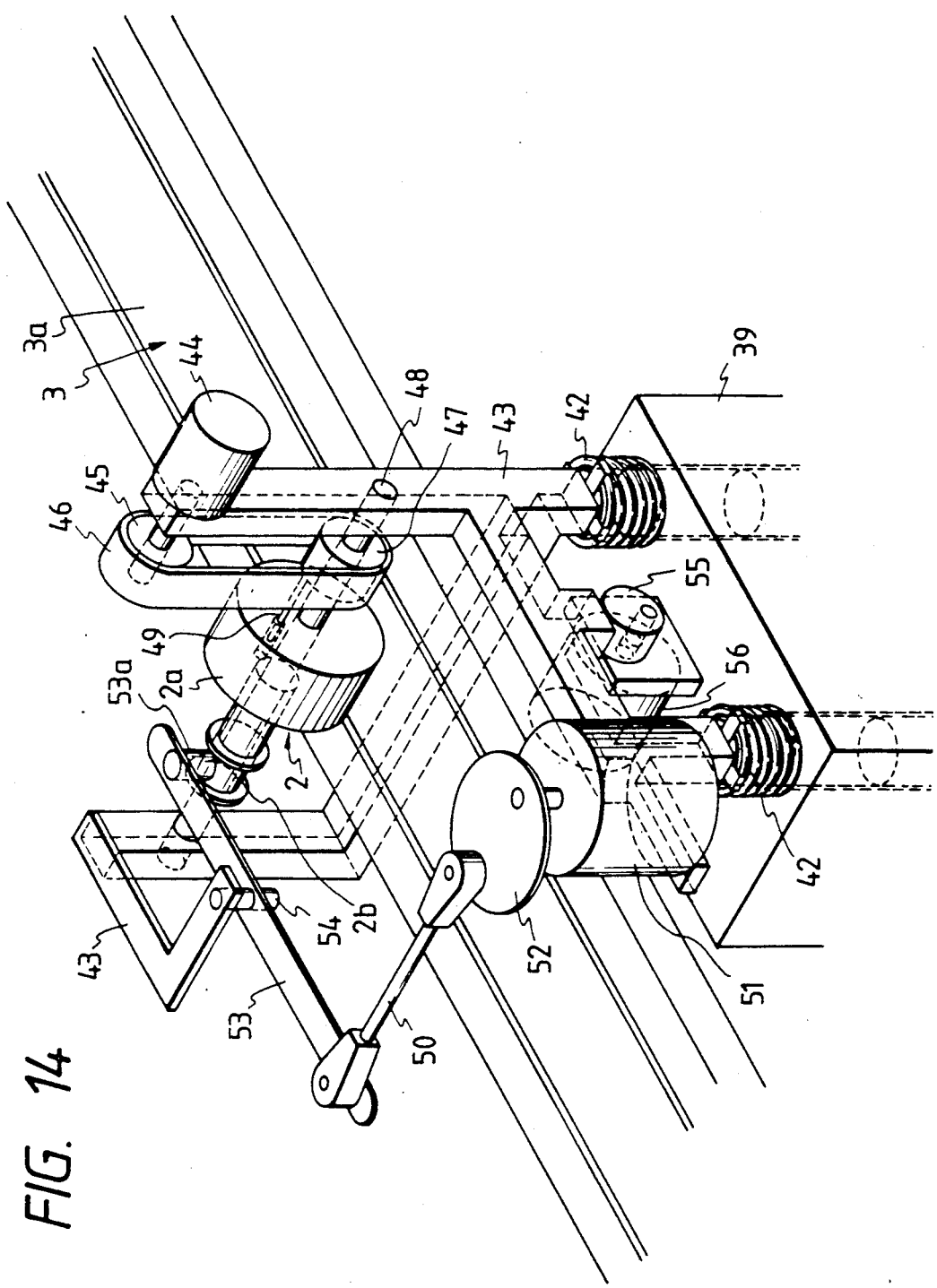
FIG. 14 is an enlarged perspective view of part of that embodiment.
Figure 15A:
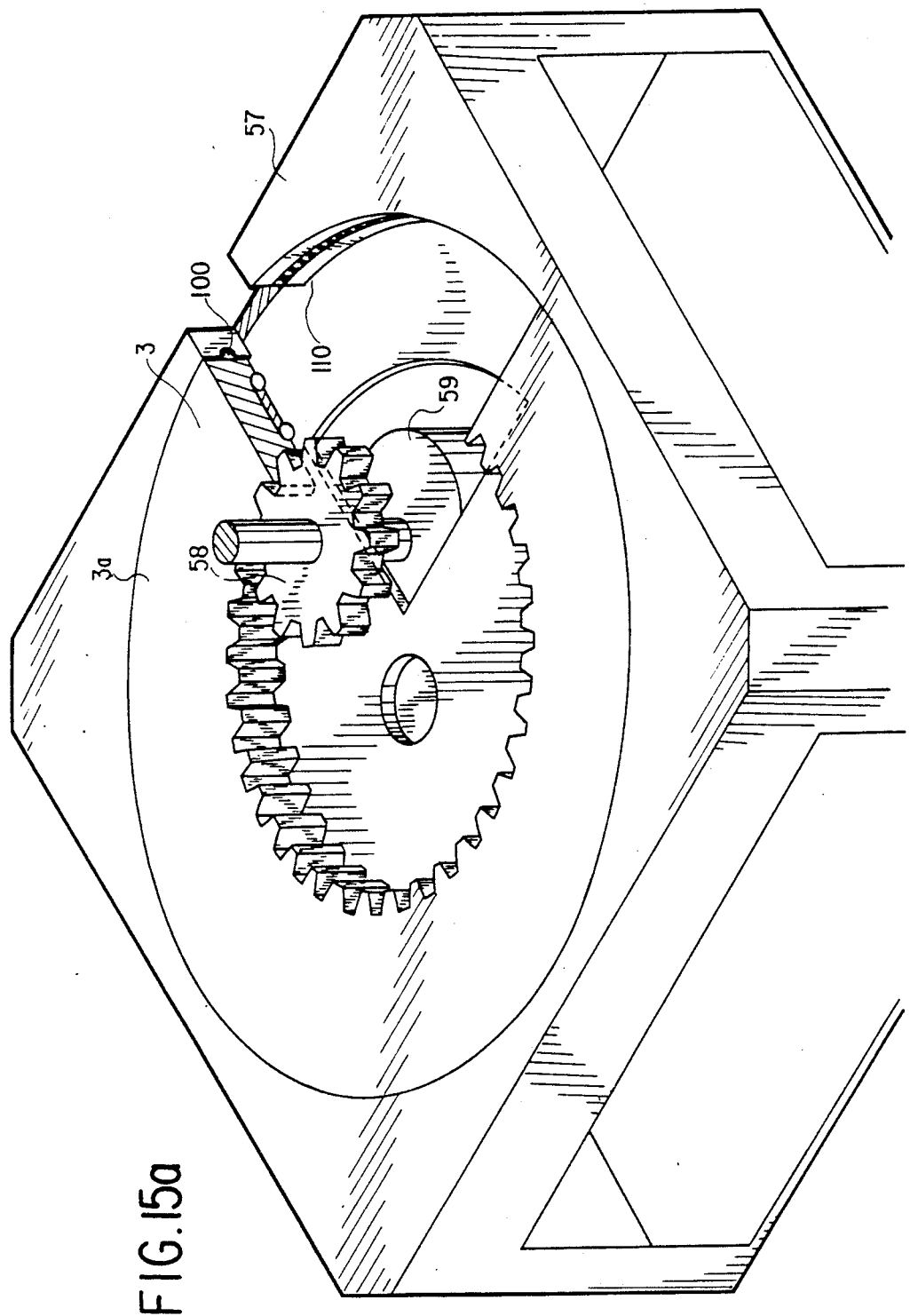
FIG. 15(a) is a further perspective view of the embodiment of FIG. 15.
Figure 16:
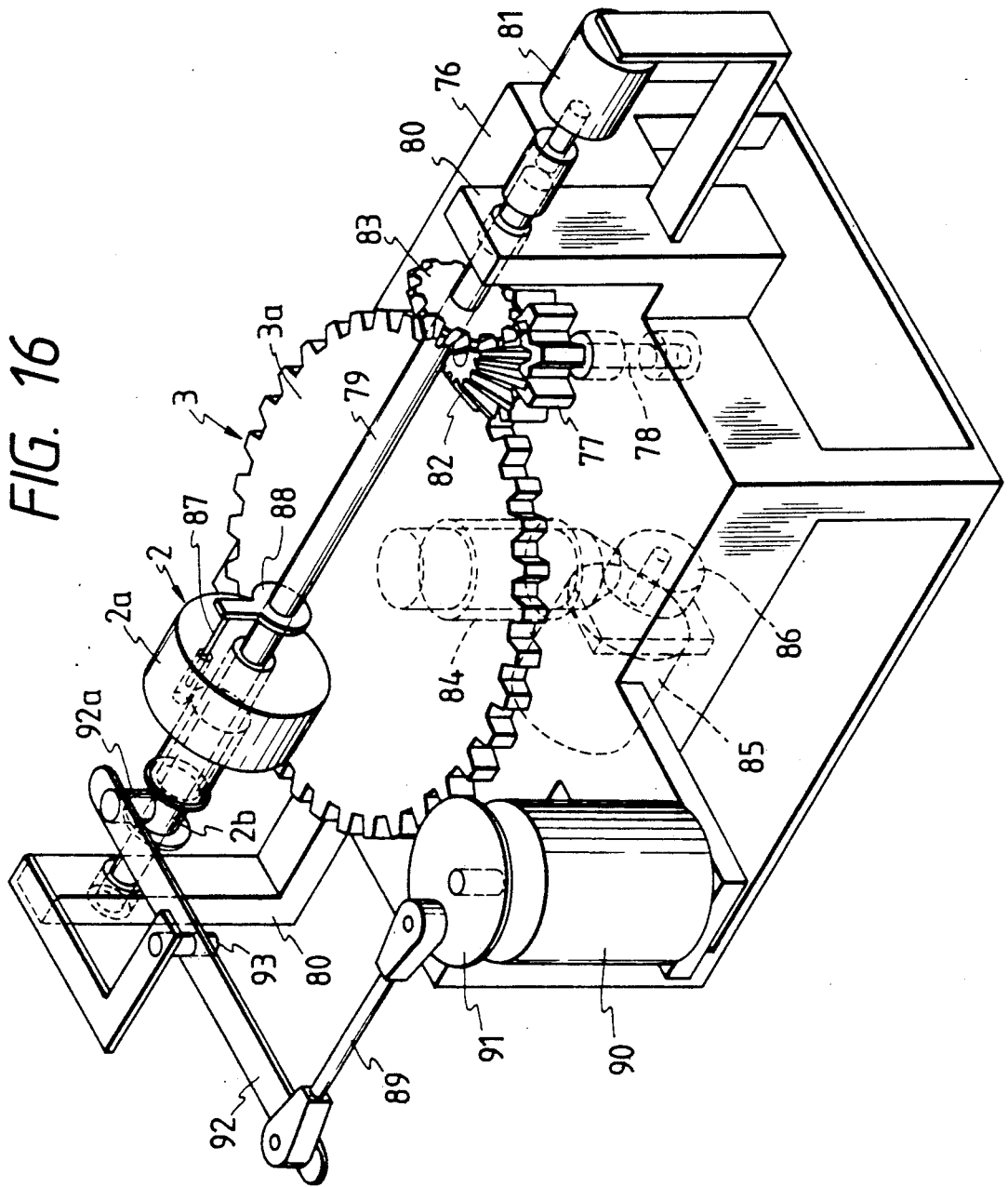
FIG. 16 is a perspective view of a still further embodiment of the apparatus for making the dental root canal filling points according to the present invention.

FIG. 9 is a perspective view of one embodiment of the apparatus for making the dental root canal filling points according to the present invention, FIG. 10 is an enlarged perspective view of part of that embodiment, FIG. 11 is a perspective view showing another embodiment of the rocking rotary member which is attached in place, FIG. 12 is a view illustrative of the initial stage of the fabrication of the dental root canal filling points with the present apparatus as shown in FIG. 9, FIG. 13 is a perspective view of another embodiment of the apparatus for making the dental root canal filling points according to the present invention, FIG. 14 is an elarged perspective view of part of the second embodiment, FIG. 15 is a perspective view of a further embodiment of the apparatus for making the dental root canal filling point according to the present invention, and FIG. 16 is a perspective view of a still further embodiment of the apparatus for producing the dental root canal filling point according to the present invention.

Throughout FIGS. 9 to 16, reference numerals 1, 2, 3 and 4 respectively stand for the dental root canal filling point in the form of an elongated cone, the rotary member having its outer processing surface 2a in the form of a curved plate parallel with its axial direction X and rotating at a predetermined speed, the moving member designed in such a way that at least its processing surface 3a is located in parallel with the processing surface 2a of the rotary member 2 and moves at a speed substantially identical with the peripheral speed of the rotary member 2 and in the same direction as that of the rotary member 2 in the gap portion in which the minimum distance is defined between the moving member and the processing surface 2a of the rotary member 2, and the rod-like material for the dental root canal filling points, all the members being of similar structures as explained in connection with said fabrication method.

Reference will now be made to the structure of the first embodiment of the present apparatus shown in FIGS. 9 to 12.

Fixedly provided on a base 5 is a framework 6, across which a shaft 7 is mounted. A belt 8 is rotatably driven by a geared pulley (a pulley with gear) 10 driven by a motor 9 placed on the base 5, and a pulley 11 is attached to the shaft 7 and driven by the movement of the belt 8. Preferably, these pulleys 10 and 11 are provided with a non-skid function on their surfaces to engage the belt 8 to prevent slippage of the belt 8 for precise transmission of the driving force of the motor 9. Preferably, the non-skid function is defined by toothed members which mesh precisely with each other and are of limited play. In order to transmit the rotational force of the pulley 11 to the moving member 3, the moving member 3 may previously be formed together with the pulley 11. Alternatively, the moving member 3 may be formed separately from and later united to the pulley 11. Further alternatively, the pulley 11 and the moving member 3 may be key-fixed to the shaft 7, or a spline shaft may be used as the shaft 7 to which the pulley 11 and the moving member 3 are attached, as is the case with the embodiment shown in FIG. 11. Where the moving member 3 is slidable along the shaft 7, use may be made of a connecting rod 12 having one end slidably inserted into the off-center position of the moving member 3 and the other end fixed at the opposite off-center position of the pulley 11, as shown in FIGS. 9 and 10, or use may be made of a spline shaft as the shaft 7, as is the case with the embodiment illustrated in FIG. 11. Moving links 13 are movable on both sides of the base 5 in a direction normal to said shaft 7. Rocking levers 14 are pivotally supported by a shaft 16 fixed to supports 15 vertically provided on both sides of the base 5, have their upper ends drawn toward the framework 6 by resilient members _17 such as tension coil springs disposed between the rocking levers and the framework 6, and are pin-jointed at their lower ends to said moving links 13. A shaft 18 is provided between the upper portions of the rocking levers 14 located on its both sides with its center being nearly flush with said shaft 7. A belt 19 is rotatably driven by a geared pulley 20 attached to a shaft 21 provided on the base 5, and said geared pulley 20 is in gear mesh with the geared pulley 10. A pulley 22 is attached to the shaft 18 and driven by the belt 19. Preferably, these pulleys 20 and 22 are provided with a non-skid function on their surfaces to engage the belt 19 to prevent slippage of the belt 19 for precise transmission of the driving force of the motor 9. Preferably, the non-skid function is defined by toothed members which mesh precisely with each other and are of limited play.

A connecting rod 23 has one end fixed at an off-center position of the pulley 22 and the other end slidably inserted into the opposite off-center position of the rotary member 2 slidably attached to the shaft 18 and slidable along the shaft 18, and is provided to transmit the rotational force of the pulley 22 to the rotary member 2. This connecting rod 23 may be dispensed with, if the shaft 18 is defined by a spline shaft, as shown in FIG. 11. A cam 24 is rotatably driven by a motor 25 placed on the base 5. A cam follower 26 is attached to a shaft 27 provided at the ends of said moving links 13 opposite to the rocking levers 14, and is designed to be in engagement with the cam 24 and be forced in operative association with the rotation of the cam 24 for moving the moving links 13 toward the rocking levers 14. A crank rod 28 is pin-jointed to a crank plate 30 fixed to the shaft of a motor 29 placed on the framework 6 (in the illustrated embodiment, it is eccentrically fixed to the shaft of the motor 29). A rocking arm 31 is pin-jointed to an extreme end of the crank rod 28, and rocks around a fulcrum 32 located on the framework 6. At equidistances from the fulcrum 32 of the rocking arm 31, there are engaging rollers 31a and 31b to engage an engaging portion 3d integral with the moving member 3 slidable along said shaft 7 and an engaging portion 2b integral with the rotary member 2 slidable along the shaft 18, so that when the motor 29 placed on the framework 6 is driven to rock the rocking arm 31 around the fulcrum 32, the moving member 3 and rotary member 2 rock at the same speed in the opposite directions. Since the desired results are obtained by rocking of the rotary member 2 alone, the engaging roller 31a of the rocking arm 31 and the engaging portion 3d of the moving member 3 may be dispensed with, if the moving member 3 does not rock. A projector 33 and a receptor 34 are arranged to provide non-contact detection of the material 4 for the dental root canal filling point when the material 4 has been supplied in the gap portion in which the minimum distance is defined between the processing surfaces 2a and 3a of the rotary member 2 and moving member 3. A guide 35 is provided to feed the material 4 for the dental root canal filling point in the gap portion in which the minimum distance is defined between the processing surfaces 2a and 3a of the rotary member 2 and moving member 3. A heating means 36 comprising a hot air nozzle is provided to inject an amount of heated air onto the material 4 for the dental root canal filling point fed by the guide 35 for heating it. As mentioned above, the heating means 36 may be an infrared lamp (not shown) for the irradiation of thermal energy beams, a built-in heater or a band heater (not shown) incorporated in the rotary member 2 and moving member 3 and brought into contact with the processing surfaces 2a and 3a through a felt, etc. A cold air nozzle 37 is provided to inject an amount of cold air onto the dental root canal filling point formed by passing through the gap portion in which the minimum distance is defined between the processing surfaces 2a and 3a of the rotary member 2 and moving member 3 for the purpose of cooling. If the material 4 for the dental root canal filling point is longer, then a grip member 38 is provided to grip on both sides the material 4 fed out of said gap portion at a given length portion, whenever the leading end, having such a given length, of the material 4 is detected by the projector 33 and receptor 34.

Reference will then be made to the structure of the second embodiment illustrated in FIGS. 13 and 14.

To shafts provided across a base 39 are attached pulleys 40, one of which is driven by a motor 41 placed on the base 39. Around and between the pulleys 40, there is the moving member 3 having its processing surface 3a in the form of a flat endless belt, said member 3 being rotatably driven thereby at a predetermined speed in a certain direction. A belt 46 is rotatably driven by a pulley 45 driven by a motor 44 placed on a framework 43 supported on the base 39 by a spring 42. A pulley 47 is attached to a shaft 48 provided across the framework 43 and having slidably mounted thereon the rotary member 2 having its outer processing surface 2a in the form of a curved plane in parallel with its axis X, and is driven by the belt 46 rotatably driven. Preferably, these pulleys 45 and 47 are provided with a non-skid function on their surfaces to engage the belt 46 to prevent slippage of the belt 46 for the precise transmission of the driving force of the motor 44. Preferably, such a non-skid function is defined by toothed members which mesh precisely with each other and are of limited play. A connecting rod 49 has one end fixed at an off-center position of the pulley 47 and the other end slidably inserted into the opposite off-center position of rotary member 2 slidably attached to the shaft 48 and slidable along said shaft 48, and is arranged to transmit the rotational force of the pulley 47 to the rotary member 2. This connecting rod 49 may be dispensed with, if the shaft 48 is defined by a spline shaft, as is the case with the embodiment illustrated in FIG. 11. A crank rod 50 is pin-jointed to a crank plate 52 fixed to the shaft of a motor 51 placed on the framework 43 (in the illustrated embodiment, it is eccentrically secured to the shaft of the motor 51). A rocking arm 53 is pin-jointed to an extreme end of the crank rod 50, and rocks around a fulcrum 54 located on the framework 43. At an extreme end of the rocking arm 53, there is provided an engaging roller 53a to engage the engaging portion 2b integral with the rotary member 2 slidable along said shaft 48, so that when the motor 51 on the framework 43 is driven to rock the rocking arm 53 around the fulcrum 54, the rotary member 2 rocks along the shaft 48. A cam 55 is attached to the shaft of a motor 56 placed on the base 39, and is engaged with the framework 43 supported on the base 39 by means of the spring 42. With the cam 55 rotated by the motor 56, there is a variation of the distance of the gap portion defined between the processing surfaces 2a and 3a of the rotary member 2 attached to the framework 43 through the shaft 48 and moving member 3.

Reference will further be made to the structure of the third embodiment illustrated in FIG. 15.

There is provided a base 57, and a lower gear 58 is fixed to the shaft of a motor 59 placed on the base 57 and .eshes with an internal gear provided in a wheel-form moving member 3 having a flat processing surface 3a. The wheel-form moving member 3 is then rotatably supported on a concave plane 100 of reduced friction, provided on the base 57 and processed or coated with a fluorocarbon resin or formed with bearings 110 as illustrated in FIG. 15 (a). Thus, with the motor 59 driven, the wheel-form moving member 3 is rotated at a predetermined speed in a certain direction. An upper gear 60 is fixed to the shaft of the motor 59 above the lower gear 58, and is in mesh with a gear 64 fixed to a shaft 63 pivotally secured on a framework 62 supported on the base 57 by a spring 61. A bevel gear 65 is attached to a shaft 66 positioned across the framework 62 and having the rotary member 2 rotatably attached thereto, and is in mesh with a bevel gear 67 fixed to said shaft 63, said bevel gear 65 being adapted to be driven by said motor 59. A connecting rod 68 has one end fixed at an off-center position of the bevel gear 65 and the other end slidably inserted into the opposite off-center position of the rotary member 2 slidably attached to the shaft 48 and slidable along said shaft 66, and is provided to transmit the rotational force of the bevel gear 65 to the rotary member 2.

This connecting rod 68 may be dispensed with, if the shaft 66 is defined by a spline shaft, as shown in FIG. 11.

A crank rod 69 is pin-jointed to a crank plate 71 secured to the shaft of a motor 70 placed on the framework 62 (in the illustrated embodiment, it is eccentrically fixed to the shaft of the motor 70). A rocking arm 72 is pin-jointed to an extreme end of the crank rod 69, and rocks around a fulcrum 73 formed on the framework 62. At an extreme end of the rocking arm 72, there is provided an engaging roller 72a to engage the engaging portion 2b integral with the rotary member 2 slidable along said shaft 66, so that when the motor 70 placed on the framework 62 is driven to rock the rocking arm 72 around the fulcrum 73, the rotary member 2 rocks along the shaft 66. A cam 74 is attached to the shaft of a motor 75 placed on the base 57, and is brought into engagement with the framework 62 supported on the base 57 by the spring 61. With the cam 74 driven by the motor 75, there is a variation of the distance of the gap portion defined between the processing surfaces 2a and 3a of the rotary member 2 and moving member 3.

Finally, the structure of the fourth embodiment illustrated in FIG. 16 will be explained.

A gear 77 is fixed to a rotatably driven shaft 78 vertically and rotatably provided on a base 76. The gear 77 is in mesh with an external gear provided on the outer face of the moving member 3, now in the form of a disc, which has its processing surface 3a in the form of a flat plane. A shaft 79 is provided across a framework 80 fixed on the base 76, said shaft 79 slidably provided with the rotary member 2 having its outer processing surface 2a in the form of a curved plane in parallel with its axial direction X. This shaft 79 is driven by a motor 81 placed on the base 76. A bevel gear 82 is fixed to said shaft 78 above the gear 77 and is in mesh with a bevel gear 83 fixed to said shaft 79, so that, when said motor 81 is driven, the disc-like moving member 3 is rotated around a central shaft at a predetermined speed in a certain direction, said central shaft being adapted to be rotatable around and vertically displaceable along a slide bearing 84 provided in a through-hole. It is to be noted that these bevel gears 82 and 83 may be dispensed with, if said shaft 78 is driven directly by a motor (not shown) placed below the base 76. A motor 85 is placed on the lower face of the base 76 and a cam 86 is brought in engagement with the central shaft of said disc-like moving member 3, so that, when the motor 85 is driven, the disc-like moving member 3 displaces vertically in conformity with the shape of the cam 86. A connecting rod 87 is provided to transmit the rotatinal force of an arm member 88 fixed to said shaft 79 to the rotary member 2, and has one end fixed to said arm member 88 and the other end slidably inserted into the opposite off-center position of the rotary member 2 slidably attached to the shaft 79 and slidable along the shaft 79. This connecting rod 87 may be dispensed with, if the shaft 79 is defined by a spline shaft, as is the case with the embodiment illustrated in FIG. 11. A crank rod 89 is pin-jointed to a crank plate 91 fixed to the shaft of a motor 90 placed on the framework 80. A rocking arm 92 is pin-jointed to an extreme end of the crank rod 89, and rocks around a fulcrum 93 formed on the framework 80. At an extreme end of the rocking arm 92, there is provided an engaging roller 92a to engage the engaging portion 2b integral with the rotary member 2 slidable along said shaft 79. As the motor 90 placed on the base 76 is driven to rock the rocking arm 92 around the fulcrum 93, the rotary member 2 rocks along the shaft 79.

Reference will in turn be made to the operation for making the dental root canal filling points with the apparatus of such structures assembled to make them according to the present invention.

Reference will first be made to the operational mode of the apparatus shown in FIGS. 9 to 12.

First, the heating means 36, e.g., a hot air nozzle is actuated to apply heat to the material 4 for the dental root canal filling point by the injection of heated air, while the cold air nozzle is previously actuated to inject coolant air for cooling the formed dental root canal filling point 1. Then, the motors 9 and 29 are driven with the power source to the motor 25 being put on along with power sources to the projector 33 and receptor 34 being held on. Whereupon, the rocking arm 31, pin-jointed to the extreme end of the crank rod 28 pin-jointed to the crank plate 30 fixed to the shaft of the motor 29, is driven and rocked by the motor 29 around the fulcrum 32 formed on the framework 6 at a speed of the order of, e.g., 50 to 1,400 r.p.m. Since the rocking arm 31 is provided with the engaging roller 31b to engage the engaging portion 2b integral with the rotary member 2 slidable along the shaft 18, the rotary member 2 rocks along the shaft 18 at an aforesaid speed. In this case, if the engaging roller 31a to engage the engaging portion 3d integral with the moving member 3 slidable along the shaft 7 is located at a position spaced by the distance equal to that from the the fulcrum 32 of the rocking arm 31 to the engaging roller 31b, then the moving member 3 and rotary member 2 rock along the shafts 7 and 18 at the same speed as mentioned above in the opposite directions. Since the desired results are obtained if the stroke of such rocking movement is 1 mm or more. Driving of the motor 9 then causes the geared pulley 10 and the geared pulley 20 in gear mesh therewith to be rotated to drive the belts 8 and 19, so that the pulleys 11 and 22 are rotated around the shafts 7 and 18. In this case, if the geared pulleys 10, 20 and the pulleys 11, 22 include the non-skid mechanisms each comprising a toothed member etc., it is then unlikely that slips may occur between the geared pulleys 10 and 20 and the pulleys 11 and 22, so that the rotations of the geared pulleys 10 and 20 can precisely be transmitted to the pulleys 11 and 22. The pulleys 11 and 22 and the moving member 3 and rotary member 2 are connected together for integral rotation by means such as the connecting rods 12 and 23 having one ends fixed to the pulleys 11 and 22 and the other ends slidably inserted into the moving and rotary members 3 and 2, or spline shafts form the shafts 7 and 18 to which the pulleys 11 and 22 are attached. Thus, while rocking along the shaft 18 (and the shaft 7) at a speed as mentioned above, the rotary member 2 (and the moving member 3) rotate at the same r.p.m. as the pulleys 11 and 22. In this state, when the material 4 for the dental root canal filling point is fed from the guide 35, that material 4 is heated and softened by the heating means 36 and, while remaining softened, is fed in the gap portion in which the minimum distance is defined between the processing surfaces 2a and 3a of the rotary member 2 and moving member 3. The material 4 is then formed into a circular shape in section conforming to the gap portion, in which the minimum distance is defined between the rotary member 2 and moving member 3, by rocking of the rotary member 2 having its processing surface 2a in parallel with its axis X and rotating at a nearly same speed or said rotary member 2 and the moving member 3 again having its processing surface 3a in parallel with its axis X and rotating at a nearly same speed.

At this time, since the light emanating from the projector 33 is cut off, the receptor 34 detects that the leading end of the material 4 for the dental root canal filling point is located in said gap portion. This then causes the motor 25 to be driven to rotate the cam 24, so that the cam follower 26 is forced by the cam in engagement therewith to move the moving links 13 toward the rocking levers 14 on the base 5 through the shaft 27. Thus, the upper ends of the rocking levers 14 pin-jointed to the moving links 13 move around the shaft 16 fixed to the supports 15 vertically provided on both sides of the base 5 against the tensile forces of the resilient members 17, so that the processing surface 2a of the rotary member 2 is spaced away from the processing surface 3a of the moving member 3, but are thereafter restored to the original states under the tensile forces of the resilient members 17. In this case, the ratio of the moving speed of the leading end of the material 4 for the dental root canal filling point brought in by the relative rotation of the rotary and moving members 2 and 3 rotating at a nearly identical speed in the opposite directions with respect to the moving speed at which the processing surface 2a of the rotary member 2 is spaced away from the processing surface 3a of the moving member 3 is continuously varied while conforming to the taper T of the dental root canal filling point 1 to be produced. In this way, while retaining a circular shape in section, the material 4 for the dental root canal filling point is formed into the dental root canal filling point 1, which has the desired taper T in its longitudinal direction. The dental root canal filling point 1 formed by passing through the gap portion in which the minimum distance is defined between the processing surfaces 2a and 3a of the rotary and moving members 2 and 3 is immediately cooled and hardened by the coolant air injected from the cold air nozzle 37, thus giving the dental root canal filling point 1, which is not easily deformed and has the desired taper T.

The foregoing explanation holds for the apparatus shown in FIGS. 9 and 12. If the rotary member 2 is defined by a cylindrical rotary body having its axis located at an off-center position as shown in FIG. 3 or a non-cylindrical rotary body whose distance from the axis to processing surface 2a varies successively as shown in FIG. 4, rather than by the cylindrical rotary body including its processing surface 2a having its center of rotation coincident with its axis, the motor 25 may then not be driven. Alternatively, the moving links 13, cam 24, motor 25, cam follower 26 and shaft 27 may be removed from the apparatus. In such a case, however, it is to be noted that the shape of the dental root canal filling points to be fabricated is predetermined due to lack of variability in the shape thereof. Accordingly, when it is intended to fabricate the dental root canal filling points 1 of various shapes and sizes, it is a prerequisite to provide for a number of cylindrical rotary bodies of varied sizes and having their axes at off-center positions and a number of non-cylindrical rotary bodies of varied sizes, whose distance from their axis to processing surfaces 2a varies successively.

The operational mode of the apparatus shown in FIGS. 13 and 14 will now be explained.

As is the case with the apparatus illustrated in FIGS. 9 to 12, such heating means as a hot air nozzle or infrared lamp, although not illustrated, is actuated to apply heat to the material 4 for the dental root canal filling point, while coolant air is previously injected from a cold air nozzle to cool the dental root canal filling point 1. Then, the motors 41, 55 and 44 are driven with the power source to the motor 56 being turned on. Whereupon, the rocking arm 53 pin-jointed to the extreme end of the crank rod 50 pin-jointed to the crank plate 52 fixed to the shaft of the motor 51 is driven and rocked by the motor 51 around the fulcrum 54 formed on the framework 43 at, e.g., 50 to 1,400 r.p.m. Since the rocking arm 53 is provided with the engaging roller 53a to engage the engaging portion 2b integral with the rotary member 2 slidable along the shaft 48, the rotary member 2 rocks along the shaft 48, correspondingly. Satisfactory results may be obtained at a stroke of such rocking of the order of 2 mm or more. Driving of the motor 41 then causes the moving member 3 provided around and between the pulleys 40 in the form of an endless belt having the flat processing surface 3a to be driven at the predetermined speed in a certain direction. Further, the pulley 45 is rotated by the motor 44 to drive the belt 46, so that the pulley 47 turns around the shaft 48. In this case, if the pulleys 45 and 47 include the non-skid functions each comprising a toothed member etc., then it is unlikely that slips may occur between the belt 46 and the pulleys 45 and 47, so that the rotation of the pulley 45 is precisely transmitted to the pulley 47. The pulley 47 and the rotary member 2 are connected together for integral rotation by such means as the connecting rod 49 having one end fixed to the pulley 47 and the other end slidably inserted into the rotary member 2, or a spline shaft forms the shaft 48 to which the pulley 47 is attached. Thus, while rocking along the shaft 48, the rotary member 2 rotates at the same r.p.m. as the pulley 47. In this state, when the material 4 for the dental root canal filling point is fed from a guide (not shown) onto the processing surface 3a of the moving member 3 in a direction almost parallel with the direction of movement of the moving member 3, that material 4 is heated and softened by the heating means and, while remaining softened, is fed in the gap portion in which the minimum distance is defined between the processing surfaces 2a and 3a of the rotary and moving members 2 and 3. The material 4 for the dental root canal filling point is then formed into a circular shape in section conforming to the gap portion, in which the minimum distance is defined between the rotary and moving members 2 and 3, by the rocking movement of the rotary member 2 having its processing surface 2a in the form of a curved plane parallel with its axial direction X. In this case, the ratio of the moving speed of the leading end of the rod-like material 4 for the dental root canal filling point brought in by the relative movement of the rotary and moving members 2 and 3 rotating and moving at a nearly identical speed with respect to the moving speed at which the processing surface 2a of the rotary member 2 attached through the shaft 48 to the framework 43 lifted up by the cam 55 rotated by the motor 56 is spaced away from the processing surface 3a of the moving member 3 is continuously varied while conforming to the taper T of the dental root canal filling point 1 to be fabricated. In this way, while retaining a circular shape in section, the material 4 for the dental root canal filling point is formed into the dental root canal filling point 1, which has the desired taper T in its longitudinal direction.

The second embodiment of the present apparatus has been described with reference to FIGS. 13 and 14. If the rotary member 2 is defined by a cylindrical rotary body having its axis located at an off-center position as illustrated in FIG. 3 (although the moving member 3 in FIG. 3 is a cylindrical rotary body, it should be construed as a flat moving body) rather than by the cylindrical rotary body including its processing surface 2a having its center of rotation coincident with its axis, a non-cylindrical rotary member whose distance from the processing surface 2a to axis varies successively as shown in FIG. 6, or a cylindrical rotary body including its processing surface 2a having its center of rotation coincident with its axis, provided that the associated moving member 3 is provided in its processing surface 3a with a groove inclining with respect to its moving direction, as shown in FIG. 7, it is then unnecessary to drive the motor 56. Alternatively, use may be made of apparatus in which the framework 43 is attached directly onto the base 39 with no provision of the spring 42, cam 55 and motor 56. With such apparatus, however, the shape of the dental root canal filling point to be fabricated must be preselected due to lack of variability in the shape thereof. Accordingly, when it is intended to make the dental root canal filling points of various shapes and sizes, it is a prerequisite to provide for a number of cylindrical rotary bodies of varied sizes and having their axis located at off-center positions and a number of non-cylindrical rotary bodies of varied sizes, whose distance from their axis to processing surfaces 2a varies successively, or a number of moving members 3 in the form of an endless belt, which are provided in their processing surfaces 3a with grooves of varied sizes and shapes, inclining with respect to their moving direction.

Reference will then be made to the operational mode of the apparatus illustrated in FIG. 15.

As is the case with the apparatus illustrated in FIGS. 9 to 12, such heating means as a hot air nozzle or infrared lamp, although not illustrated, is actuated to apply heat to the material 4 for the dental root canal filling point, while coolant air is injected from a cold air nozzle for cooling the dental root canal filling point 1 fabricated. Then, the motors 59 and 70 are driven with the power source to the motor 75 being turned on. Whereupon, the rocking arm 72 pin-jointed to the extreme end of the crank rod 69 pin-jointed to the crank plate 71 fixed to the shaft of the motor 70 is driven and rocked by the motor 70 around the fulcrum 73 formed on the framework 62 at, e.g., 50 to 1,400 r.p.m. Since the rocking arm 72 is provided with the engaging roller 72a to engage the engaging portion 2b integral with the rotary member 2 slidably along the shaft 66, the rotary member 2 rocks along the shaft 66, correspondingly. Sufficient results are obtained, if the stroke of such rocking is of the order of 2 mm or more. By driving of the motor 59, the moving member 3 in the form of a wheel having its internal gear in mesh with the lower gear 58 attached to the shaft of the motor 59 is rotated at the predetermined speed in a certain direction, and the bevel gear 67 is rotated, which is attached to the shaft 63 rotated by the gear 64 in mesh with the upper gear 60 attached to the shaft of the motor 59, so that the bevel gear 65 in mesh with the bevel gear 67 rotates around the shaft 66 pivotally supported on the framework 62. The bevel gear 65 and the rotary member 2 are connected together for integral rotation by such means as the connecting rod 68 having one end fixed to the bevel gear 65 and the other end slidably inserted into the rotary member 2, or the shaft 66 having the bevel gear 65 attached thereto is formed of a spline shaft. Thus, while rocking along the shaft 66, the rotary member 2 rotates as the same r.p.m. as the bevel gear 65. In this state, when the material 4 for the dental root canal filling point is supplied from a guide (not shown) onto the processing surface 3a of the moving member 3 in the direction of movement of the moving member 3, namely, a direction nearly parallel with the circumferential direction of the wheel, that material 4 is heated and softened by the heating means and, while remaining softened, it is fed in the gap portion in which the minimum distance is defined between the processing surfaces 2a and 3a of the rotary and moving members 2 and 3. The material 4 is then formed into a circular shape in section conforming to the gap portion, in which the minimum distance is defined between the rotary member 2 and moving member 3, by the rocking movement of the rotary member 2 having its processing surface 2a in parallel with its axial direction X. In this case, the ratio of the moving speed of the leading end of the rod-like material 4 for the dental root canal filling point brought in by the relative movement of the rotary and moving members 2 and 3 rotating and moving at a nearly same speed with respect to the moving speed at which the processing surface 2a of the rotary member 2 attached through the shaft 66 to the framework 62 lowered by the cam 74 rotated by the driving motor 75 is spaced away from the processing surface 3a of the moving member 3 is continuouslsy varied while conforming to the taper T of the dental root canal filling point 1 to be fabricated. In this way, while retaining a circular shape in section, the material 4 for the dental root canal filling point is formed into the dental root canal filling point 1, which has now the desired taper T in its longitudinal direction.

The foregoing explanation applies to the operational mode of the apparatus illustrated in FIG. 15. If the rotary member 2 is defined by a cylindrical rotary body having its axis located at an off-center position as shown in FIG. 3 (although the moving member 3 in FIG. 3 is a cylindrical rotary member, it must be construed as a flat moving body), rather than by the cylindrical rotary body including its processing surface 2a having its center of rotation coincident with its axis, a non-cylindrical rotary member whose distance from the aixs to processing surface 2a varies successively as shown in FIG. 6, or a cylindrical rotary body including its processing surface 2a having its center of rotation coincident with its axis, provided that the associated moving member 3 is provided in its processing surface 3a with a groove inclining with respect to its moving direction, as shown in FIG. 7, it is then unnecessary to drive the motor 75. Alternatively, use may be made of appartaus in which the framework 62 is fixed directly to the base 57 with no provision of the spring 61, cam 74 and motor 75. With such apparatus, however, the shape of the dental root canal filling point to be fabricated must be preselected due to lack of variability in the size thereof. Accordingly, when it is intended to fabricate the dental root canal filling points of various shapes and sizes, it is a prerequisite to provide for a number of cylindrical rotary bodies of varied sizes and having their axis located at off-center positions and a number of non-cylindrical rotary bodies of varied sizes, whose distance from their axis to processing surfaces 2a varies successively, or a number of moving members 3 in the form of a wheel, which are provided in their processing surfaces 3a with grooves of varied sizes and shapes, inclining with respect to their moving direction.

The operational mode of the apparatus shown in FIG. 16 will finally be explained.

As is the case with the apparatus illustrated in FIGS. 9 to 12, such heating means as a hot air nozzle or infrared lamp, although not illustrated, is actuated to apply heat to the material 4 for the dental root canal filling point, while coolant air is injected from a cold air nozzle for cooling the dental root canal filling point 1 fabricated. Then, the motors 81 and 90 are driven with the power source to the motor 85 being turned on. Whereupon, the rocking arm 92 pin-jointed to the extreme end of the crank rod 89 pin-jointed to the crank plate 91 fixed to the shaft of the motor 90 is driven and rocked by the motor 90 around the fulcrum 93 formed on the framework 80 at, e.g., 50 to 1,400 r.p.m. Since the rocking arm 92 is provided with the engaging roller 92a to engage the engaging portion 2b integral with the rotary member 2 slidable along the shaft 79, the rotary member 2 rocks along the shaft 79, correspondingly. Sufficient results are obtained, if the stroke of such rocking is of the order of 2 mm or more. In the illustrated embodiment, driving of the motor 81 then causes the rotation of the bevel gear 83 attached to the shaft 79 rotated thereby and, in turn, the rotation of the bevel gear 82 fixed to the shaft 78 vertically provided on the base 76 and in mesh with the bevel gear 83, so that the disc-like moving member 3 having its external gear in mesh with the gear 77 fixed to the shaft 78 is rotated around its axis at the predetermined speed in a certain direction.

However, even when the shaft 78 vertically provided on the base 76 is directly driven by a motor (not shown) disposed below the base 76 in a state where the bevel gear 82 fixed to that shaft 78 and the bevel gear 83 attached to the shaft 79 are removed, the disc-like moving member 3 having its external gear in mesh with the gear 77 fixed to the shaft 78 is rotated around its axis at the predetermined speed in a certain direction. Further, the shaft 79 driven by the motor 81 is fixedly provided with an arm member 88. The arm member 88 and the rotary member 2 are connected together for integral rotation by such means as the connecting rod 87 having one end fixed to the arm member 88 and the other end slidably inserted into the rotary member 2, or the shaft 79 slidably attached to the rotary member 2 is formed of a spline shaft. Thus, while rocking along the shaft 79, the rotary member 2 rotates at the same speed in terms of r.p.m. as that of the speed of the shaft 79. In this state, when the material 4 for the dental root canal filling point is supplied from a guide (not shown) onto the processing surface 3a of the moving member 3 in the direction of movement of the moving member 3, namely, a direction nearly parallel with the circumferential direction of the disc, that material 4 is heated and softened by the heating means and, while remaining softened, it is fed in the gap portion in which the minimum distance is defined between the processing surfaces 2a and 3a of the rotary member 2 and moving member 3. The material 4 is then formed into a circular shape in section conforming to the gap portion, in which the minimum distance is defined between the rotary member 2 and moving member 3, by the rocking movement of the rotary member 2 having its processing surface 2a in parallel with its axial direction X. In this case, the ratio of the moving speed of the leading end of the rod-like material 4 for the dental root canal filling point brought in by the relative movement of the rotary member 2 and moving member 3 rotating and moving at a nearly identical speed with respect to the moving speed at which the processing surface 2a of the rotary member 2 attached in place through the shaft 79 is spaced away from the processing surface 3a of the moving member 3, said moving member 3 being now lowered owing to its central shaft being in engagement with the cam 86 rotated by the motor 85, is continuously varied while conforming to the taper T of the dental root canal filling point 1 to be fabricated. In this way, while retaining a circular shape in section, the material 4 for the dental root canal filling point is formed into the dental root canal filling point 1, which has now the desired taper T in its longitudinal direction.

The foregoing explanation applies to the operational mode of the apparatus illustrated in FIG. 16. If the rotary member 2 is defined by a cylindrical rotary body having its axis located at an off-center position as shown in FIG. 3 (although the moving member 3 in FIG. 3 is a cylindrical rotary member, it must be construed as a flat moving body) rather than by the cylindrical rotary body including its processing surface 2a having its center of rotation coincident with its axis, a non-cylindrical rotary member whose distance from its aixs to processing surface 2a varies successively as shown in FIG. 6, or a cylindrical rotary body including its processing surface 2a having its center of rotation coincident with its axis, provided that the associated moving member 3 is provided in its processing surface 3a with a groove inclining with respect to its moving direction, as shown in FIG. 7, it is then unnecessary to drive the motor 85. Alternatively, use may be made of apparatus in which the motor 85 and cam 86 are removed. With such apparatus, however, the shape of the dental root canal filling point to be fabricated must be preselected due to lack of variability in the shape thereof. Accordingly, when it is intended to fabricate the dental root canal filling point 1 of various shapes and sizes, it is a prerequisite to provide for a number of cylindrical rotary bodies of varied sizes and having their axis located at off-center positions and a number of non-cylindrical rotary bodies of varied sizes, whose distance from their axis to processing surfaces 2a varies successively, or a number of disc-like moving members 3; which are provided on their processing surfaces 3a with grooves of varied sizes and shapes, inclining with respect to their moving direction.

As mentioned in the preamble, there are numerous types of dental root canal filling points which should meet much severer requirements for the dimensional tolerance of their diameters and vary in diameter from the minimum 0.1 mm to the maximum 1.5 mm in the length range of 10 to 35 mm. Nonetheless, they have conventionally been manually fabricated only by those versed in the art, implying that it is necessary to train those unskilled in the art and that an increased demand with recent advancement of dental treatments is not supplied. However, the present invention makes it possible to fabricate the dental root canal filling points by inexpensive and efficient mechanical means and so makes a breakthrough in the art. The apparatus for making the dental root canal filling points according to the present invention is provided to carry out the method of the present invention, as detailed above. Typically, the present apparatus comprises in combination driving sources for a cylindrical rotary member having its processing surface in the form of a curved plane in parallel with its axial direction and rotating at a predetermined speed and a moving member having its processing surface moving at a speed nearly same to a peripheral speed of the cylindrical rotary member in the same direction as the rotational direction of the rotary member and in the form of a cylindrical or flat plane, a driving source for rocking at least the rotary member in its axial direction, and a driving source designed in such a way that, while a gap portion in which a minimum distance is defined between the processing surfaces of the rotary and moving members is held in a substantially identical plane, a ratio of a moving speed of the leading end of a rod-like material for the dental root canal filling point fed and brought in said gap portion by the rotation of the rotary member and the movement of the moving member with respect to a moving speed at which the rotary and moving members are spaced away from each other being continuously varied such that it conforms to a taper of the dental root canal filling point to be produced. Where the respective driving sources are separately provided, it is easy to operate and adjust the respective driving elements and accommodate to the production of the dental root canal filling points which vary in size and shape. If the driving source for continuously varying the speed ratio as referred to just above is not actuated, a cylindrical rotary member having its axis located at an off-center position or whose distance from the axis to processing surface varies successively may be used as the rotary member rotating at a predetermined speed, or a moving member having its processing surface provided therein with a groove inclining with respect to its moving direction may be used as the moving member, whereby it is possible to make the dental root canal filling points of the given size and shape. With such apparatus for carrying out the present method, 95% or more of the resulting products can be accepted and a length of processing time per product can be reduced by about half as compared with manual modes of operation. If the width of the processing surfaces of the rotary and moving members is increased in parallel with their axial directions, it is then possible to make a number of the dental root canal filling points at a time.

Especially when a belt or flat member driven along a cylindrical rotary member in the tangential direction is used as the moving member, the dental root canal filling point, fabricated and fed out, remains in the constant moving direction, so that the subsequent operations become very simple. If provision is made of a cold air nozzle to inject coolant air to the dental root canal filling point, as formed by passing through the gap portion in which the minimum distance is defined between the processing surfaces of the rotary and moving members, then the product is already hardened with no fear of failure or bending of its this gap in its leading end. Because of being able to be carried out and operated entirely unattended, the present apparatus and method offer no health problem. Thus, the present invention is of great industrial value.

What is claimed is:

1. Apparatus for making dental root canal filling points, which comprises in combination:
   a first belt driven by a first geared pulley driven by a first motor placed on a base;
   a third pulley attached to a first shaft provided across a framework fixed onto said base and driven by the movement of said first belt;
   a moving member attached to said first shaft and having an outer processing surface in the form of a curved plane, said curved plane being parallel with an axial direction of said moving member and being rotatable together with said third pulley;
   a second belt driven by a second geared pulley attached to a second shaft provided across said base, said second geared pulley being in gear mesh with said first geared pulley;

moving links positioned on both sides of said base and operatively connected to a cam follower, said cam follower being in engagement with a cam, said cam being rotatably driven by a second motor placed on said base, wherein rotation of said second motor causes rocking of said moving links on both sides of said base in a direction normal to said first shaft;

rocking levers pivotally supported by a third shaft fixed to supports vertically arranged on both sides of said base, upper ends of said rocking levers being biased toward said framework by resilient members provided between said framework and said rocking levers, a fourth shaft is provided between said rocking levers, said rocking levers being pivotally connected at their lower ends to said moving links, a fourth pulley attached to said fourth shaft being centrally located at a height substantially the same to that of said first shaft, and said fourth pulley being driven by said second belt;

a rotary body slidably attached to said fourth shaft and having an outer processing surface in the form of a curved plane in parallel with an axial direction of said rotary body and rotatable with said fourth pulley; and an engaging roller provided on a rocking arm and pivotally connected to an extreme end of a crank rod which is pivotally connected to a crank plate, said crank plate being fixed to shaft of a third motor placed on said framework, and adapted to rock around a fulcrum formed on said framework, said engaging roller being engaging an engaging portion integral with said rotary member.

2. Apparatus for making dental root canal filling points as claimed in claim 1, wherein said rotary member and said moving member are cylindrical rotary bodies each having its center of rotation coincident with its axis.

3. Apparatus for making dental root canal filling points as claimed in claim 1, wherein said rotary member is a cylindrical rotary body having its center of rotation coincident with its axis, and said moving member is a belt driven along a cylindrical rotary body having its center of rotation coincident with its axis.

4. Apparatus for making dental root canal filling points as claimed in claim 1, wherein said rotary member is a cylindrical rotary body having its rotational axis located at an off-center position, and said moving member is a cylindrical rotary body having its center of rotation coincident with its axis.

5. Apparatus for making dental root canal filling points as claimed in claim 1, wherein said rotary member is a non-cylindrical rotary body whose distance from its rotational axis to said outer processing surface varies successively, and said moving member is a cylindrical rotary body having its center of rotation coincident with its axis.

6. Apparatus for making dental root canal filling points as claimed in any one of claims 1 to 5, wherein said first and second geared pulleys and said third and fourth pulleys each include a non-skid means in mesh with a toothed member formed on the inner face of each of said first and second belts.

7. Apparatus for making dental root canal filling points as claimed in claim 4, wherein said rotary member is a rotary body to which a rotational force of said second pulley is transmitted through a connecting rod having one end slidably inserted into the off-center position of said rotary member and the other end fixed at a corresponding off-center position of said fourth pulley.

8. Apparatus for making dental root canal filling points as claimed in claim 6, wherein said rotary member is a rotary body which is splined connected to said fourth shaft, thereby transmitting the rotational force of said fourth pulley thereto.

9. Apparatus for making dental root canal filling points as claimed in claim 8, wherein heating means is provided to apply heat to a material for said dental root canal filling point which is to be fed in a gap portion in which a minimum distance is defined between said processing surfaces of said rotary member and said moving member.

10. Apparatus for making dental root canal filling points as claimed in claim 9, wherein said heating means for heating said material for said dental root canal filling point is a hot air nozzle with a built-in heater for injecting heated air to said fed in material (4).

11. Apparatus for making dental root canal filling points as claimed in claim 9, wherein said heating means for heating said material for said dental root canal filling point is an infrared lamp for applying thermal energy to said fed in material.

12. Apparatus for making dental root canal filling points as claimed in claim 9, wherein said heating means for heating said material for said dental root canal filling point is said rotary member and said moving member whose processing surfaces are heated.

13. Apparatus for making dental root canal filling points as claimed in claim 12, wherein a cold air nozzle is provided to inject coolant air onto said dental root canal filling point, which has been formed by passing through said gap portion in which said minimum distance is defined between said processing surfaces of said rotary member and said moving member.

14. Apparatus for making dental root canal filling points as claimed in claim 13, wherein a projector and a receptor are provided to detect in a non-contact fashion that said material for said dental root canal filling point is brought in by the relative rotation of said rotary member and said moving member and reaches said gap portion in which said minimum distance is defined between said processing surfaces of said rotary member and said moving member, thereby actuating said second motor (25).

15. Apparatus for making dental root canal filling points as claimed in claim 14, wherein upon the leading end of said material for said dental root canal filling point being detected by said projector and said receptor, a grip member is actuated to grip said material on both its sides, said grip member being located at a position spaced away by a given distance from said gap portion in which said minimum distance is defined between said processing surfaces of said rotary member and said moving member.

16. Apparatus for making a dental root canal filling point, which comprises in combination:
first and second pulleys attached to shafts and provided across a base;
a first motor placed on said base for driving one of said first and second pulleys;
a moving member in the form of a flat endless belt provided around and between said first and second pulleys and having a processing surface in the form of a flat plane;

a first shaft provided across a framework supported on said base by a spring and slidably provided with a rotary member having an outer processing surface in the form of a curved plane parallel with an axial direction of said rotary member;

a third pulley attached to said first shaft, driven by a second motor placed on said framework and rotatable together with said rotary member;

a cam mounted on a third motor placed on said base and in engagement with the same framework; and an engaging roller provided on a rocking arm and pivotally connected to an extreme end of a crank rod which is pivotally connected to a crank plate fixed to a shaft of a fourth motor placed on said framework, and adapted to rock around a fulcrum formed on said framework, said engaging roller (53a) engaging an engaging portion integral with said rotary member.

17. Apparatus for making dental root canal filling points as claimed in claim 16, wherein said rotary member is a cylindrical rotary body having its center of rotation coincident with its axis, and said moving member has its processing surface in the form of a completely flat plane.

18. Apparatus for making dental root canal filling points as claimed in claim 16, wherein said rotary member is a cylindrical rotary body having its rotational axis located at an off-center position, and said moving member has its processing surface in the form of a completely flat plane.

19. Apparatus for making dental root canal filling points as claimed in claim 16, wherein said rotary member is a non-cylindrical rotary body whose distance from its rotational axis to its processing surface varies successively, and said moving member has its processing surface in the form of a completely flat plane.

20. Apparatus for making dental root canal filling points as claimed in claim 16, wherein said rotary member is a cylindrical rotary body having its center of rotation coincident with its axis, and said moving member has its processing surface in the form of a flat plane provided therein with a groove inclining in the direction of movement of said moving member.

21. Apparatus for making dental root canal filling points as claimed in any one of claims 16 to 20, wherein a fourth pulley is driven directly by said second motor, said third pulley and said fourth pulley each including non-skid means in mesh with a non-skid toothed member formed on an inner face of a belt (46) provided between said third and fourth pulleys.

22. Apparatus for making dental root canal filling points as claimed in claim 18, wherein said rotary member is a rotary body to which a rotational force of said third pulley is transmitted through a connecting rod having one end slidably inserted into the off-center position of said rotary member and the other end fixed at a corresponding off-center position of said third pulley.

23. Apparatus for making dental root canal filling points as claimed in claim 21, wherein said rotary member is a rotary body which is splined connected to said first shaft, thereby transmitting a rotational force of said third pulley thereto.

24. Apparatus for making a dental root canal filling point, which comprises in combination:

a lower gear fixedly provided to a shaft of a first motor placed on a base;

a moving member having an inner face with an internal gear formed on said inner face, said internal gear being in mesh with said lower gear, rotatably supported in a concave plane formed on said base and having a processing surface in the form of an annulus;

an upper gear meshing with a gear fixedly mounted on a first shaft pivotally supported on a framework supported on said base by a spring and fixedly mounted on the shaft of said first motor above said lower gear;

a first bevel gear attached to a second shaft provided across said framework, said second shaft slidably provided with a rotary member having an outer processing surface in the form of a curved plane parallel to an axial direction of said rotary member, said first bevel gear meshing with a second bevel gear fixedly mounted to said first shaft for rotation integral with said rotary member;

a cam attached to a second motor placed on said base and in engagement with the framework; and an engaging roller provided on a rocking arm which is pivotally connected to an extreme end of a crank rod which is pivotally connected to a crank plate fixed to a shaft of a third motor placed on said framework for rocking around a fulcrum formed on said framework, said engaging roller engaging an engaging portion integral with said rotary member.

25. Apparatus for making dental root canal filling points as claimed in claim 24, wherein said rotary member is a cylindrical rotary body having its center of rotation coincident with its axis, and said moving member has its processing surface in the form of a completely flat plane.

26. Apparatus for making dental root canal filling points as claimed in claim 24, wherein said rotary member is a cylindrical rotary body having its rotational axis located at an off-center position, and said moving member has its processing surface in the form of a completely flat plane.

27. Apparatus for making dental root canal filling points as claimed in claim 24, wherein said rotary member is a non-cylindrical rotary body whose distance from its rotational axis to its processing surface varies successively, and said moving member has its processing surface in the form of a completely flat plane.

28. Apparatus for making dental root canal filling points as claimed in claim 24, wherein said rotary member is a cylindrical rotary body having its center of rotation coincident with its axis, and said moving member has its processing surface in the form of a flat plane provided therein with a groove inclining in the direction of movement of said moving member.

29. Apparatus for making dental root canal filling points as claimed in any one of claims 24 to 28, wherein said rotary member is a rotary body to which a rotational force of said first bevel gear is transmitted through a connecting rod having one end slidably inserted into an off-center position of said rotary member and the other end fixed at a corresponding off-center position of said first bevel gear.

30. Apparatus for making dental root canal filling points as claimed in any one of claims 24 to 28, wherein said rotary member is a rotary body which is spline connected to said second shaft, thereby transmitting the rotational force of said first bevel gear thereto.

31. Apparatus for making dental root canal filling points as claimed in claim 30, wherein said concave plane of said base, on which said moving member is rotatably supported, is coated with a fluorocarbon resin.

32. Apparatus for making dental root canal filling points as claimed in claim 30, wherein the concave plane of said base, on which said moving member is rotatably supported, is provided with a bearing.

33. Apparatus for making a dental root canal filling point, which comprises in combination:

a gear fixed to a first shaft vertically and rotatably provided on a base for driving rotation;

a moving member having a central shaft which is operatively connected to a slide bearing for rotational and vertical movements, said slide bearing being formed in a through-hole located on said base, said moving member having an outer surface which is provided with an external gear in mesh with said gear and having a processing surface in the form of a flat disc;

a second shaft driven by a first motor placed on said base, which is provided across a framework fixed onto said base, said second shaft slidably provided with a rotary member having an outer processing surface in the form of a curved plane parallel with an axial direction of said rotary member;

a cam fixed to a shaft of a second motor placed on a lower face of said base and brought into engagement with the central shaft of said moving member; and an engaging roller provided on a rocking arm which is pivotally connected to an extreme end of a crank rod which is pivotally connected to a crank plate fixed to a shaft of a third motor placed on said base for rocking around a fulcrum formed on a framework, said engaging roller engaging an engaging portion integral with said rotary member.

34. Apparatus for making dental root canal filling points as claimed in claim 33, wherein said rotary member is a cylindrical rotary body having its center of rotation coincident with its axis, and said moving member has its processing surface in the form of a completely flat plane.

35. Apparatus for making dental root canal filling points as claimed in claim 33, wherein said rotary member is a cylindrical rotary body having its rotational axis located at an off-center position, and said moving member has its processing surface in the form of a completely flat plane.

36. Apparatus for making dental root canal filling points as claimed in claim 33, wherein said rotary member is a non-cylindrical rotary body whose distance from its rotational axis to its processing surface varies successively, and said moving member has its processing surface in the form of a completely flat plane.

37. Apparatus for making dental root canal filling points as claimed in claim 33, wherein said rotary member is a cylindrical rotary body having its center of rotation coincident with its axis, and said moving member has its processing surface in the form of a flat plane provided therein with a groove inclining in the direction of movement of said moving member.

38. Apparatus for making dental root canal filling points as claimed in any one claims 33 to 37, wherein said first shaft vertically provided on said base for rotation is driven and rotated by a fourth motor placed below said base.

39. Apparatus for making dental root canal filling points as claimed in any one of claims 33 to 37, wherein said first shaft vertically provided on said base for rotation is driven and rotated by first a bevel gear in mesh with a second bevel gear mounted on said second shaft provided across said framework.

40. Apparatus for making dental root canal filling points as claimed in claim 35, wherein said rotary member is a rotary body to which a rotational force of an arm member is transmitted through a connecting rod having one end slidably inserted in an off-center position of said rotary member and the other end fixed to said arm member.

41. Apparatus for making dental root canal filling points as claimed in claim 39, wherein said rotary member is a rotary body which is splined connected to said second shaft, thereby transmitting the rotational force of said first motor thereto.

* * * * *